(12) United States Patent
Srivastava et al.

(10) Patent No.: US 12,702,835 B2
(45) Date of Patent: Aug. 11, 2026

(54) CLOUD-BASED SENSOR OPERATION ADAPTED TO PATIENT BEHAVIOR

(71) Applicant: Boston Scientific Neuromodulation Corporation, Valencia, CA (US)

(72) Inventors: Kyle Harish Srivastava, Saint Paul, MN (US); Matthew Lee McDonald, Glendale, CA (US); Rex James Woon, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 468 days.

(21) Appl. No.: 17/845,744

(22) Filed: Jun. 21, 2022

(65) Prior Publication Data

US 2022/0401739 A1 Dec. 22, 2022

Related U.S. Application Data

(60) Provisional application No. 63/213,093, filed on Jun. 21, 2021.

(51) Int. Cl.
*A61N 1/36* (2006.01)
*A61N 1/378* (2006.01)

(52) U.S. Cl.
CPC ..... *A61N 1/36139* (2013.01); *A61N 1/36071* (2013.01); *A61N 1/378* (2013.01)

(58) Field of Classification Search
CPC . A61N 1/36139; A61N 1/36071; A61N 1/378
See application file for complete search history.

(56) References Cited

U.S. PATENT DOCUMENTS 6,730,024 B2 5/2004 Freyre et al.
7,650,184 B2 1/2010 Walter (Continued)

FOREIGN PATENT DOCUMENTS

AU 2022299056 B2 5/2025
WO WO-2016151494 A1 9/2016

(Continued)

OTHER PUBLICATIONS

"U.S. Appl. No. 17/845,726, Restriction Requirement mailed Sep. 6, 2024", 8 pgs.

(Continued)

*Primary Examiner* — William J Levicky
*Assistant Examiner* — Willow Grace Welch
(74) *Attorney, Agent, or Firm* — Schwegman Lundberg & Woessner, P.A.

(57) ABSTRACT

Systems, devices, and methods for remote monitoring and managing of patients with chronic pain are discussed. A remote monitoring system comprises one or more sensors to sense physiological or functional information from the patient, a cloud-computing device communicatively coupled to the one or more sensors, and a remote device. The cloud-computing device receives patient data including physiological or functional information, and provides on-demand cloud-based services including storing the received patient data in a cloud storage, detecting a patient behavior, and generating a sensor operation recommendation based on the detected patient behavior. The remote device can access the cloud storage and the cloud-based services, and adjust operations of the one or more sensors in accordance with the sensor operation recommendation.

20 Claims, 11 Drawing Sheets

(56) References Cited

U.S. PATENT DOCUMENTS

| | | | | |
|---|---|---|---|---|
| 8,019,439 | B2 | 9/2011 | Kuzma et al. | |
| 2002/0013516 | A1 | 1/2002 | Freyre et al. | |
| 2011/0172744 | A1* | 7/2011 | Davis | A61N 1/3614 607/62 |
| 2015/0186602 | A1 | 7/2015 | Pipke et al. | |
| 2017/0000422 | A1 | 1/2017 | Moturu et al. | |
| 2017/0095670 | A1* | 4/2017 | Ghaffari | A61M 21/02 |
| 2017/0156662 | A1 | 6/2017 | Goodall et al. | |
| 2017/0196458 | A1* | 7/2017 | Ternes | A61B 7/023 |
| 2018/0008191 | A1 | 1/2018 | Cronin et al. | |
| 2018/0015284 | A1 | 1/2018 | Coleman et al. | |
| 2018/0070824 | A1* | 3/2018 | Cronin | A61B 5/02055 |
| 2018/0113172 | A1* | 4/2018 | Cronin | G06Q 10/109 |
| 2018/0185651 | A1 | 7/2018 | Astrom et al. | |
| 2018/0192943 | A1 | 7/2018 | Annoni et al. | |
| 2018/0193644 | A1 | 7/2018 | Annoni et al. | |
| 2018/0229040 | A1 | 8/2018 | Srivastava et al. | |
| 2018/0336970 | A1 | 11/2018 | Sherwood et al. | |
| 2019/0022397 | A1* | 1/2019 | Srivastava | A61N 1/36139 |
| 2019/0069245 | A1* | 2/2019 | Miller | A61B 5/4875 |
| 2019/0344080 | A1 | 11/2019 | Mcdonald et al. | |
| 2020/0101302 | A1 | 4/2020 | Huertas Fernandez et al. | |
| 2021/0060343 | A1 | 3/2021 | Srivastava et al. | |
| 2021/0178164 | A1 | 6/2021 | Srivastava et al. | |
| 2022/0400952 | A1 | 12/2022 | Srivastava et al. | |
| 2024/0242825 | A1 | 7/2024 | Calle et al. | |

FOREIGN PATENT DOCUMENTS

| | | | |
|---|---|---|---|
| WO | WO-2022271706 | A1 | 12/2022 |
| WO | WO-2022271710 | A1 | 12/2022 |

OTHER PUBLICATIONS

"Australian Application Serial No. 2022296509, First Examination Report mailed Sep. 25, 2024", 3 pgs.

"Australian Application Serial No. 2022299056, First Examination Report mailed Sep. 30, 2024", 3 pgs.

"European Application Serial No. 22744023.7, Response to Communication Pursuant to Rules 161(1) and 162 filed Jul. 26, 2024", 10 pgs.

"European Application Serial No. 22744024.5, Response to Communication Pursuant to Rules 161(1) and 162 filed Jul. 31, 2024", 10 pgs.

"International Application Serial No. PCT/US2022/034353 International Search Report mailed Dec. 13, 2022", 6 pgs.

"International Application Serial No. PCT/US2022/034353 Written Opinion mailed Dec. 13, 2022", 11 pgs.

"International Application Serial No. PCT/US2022/034353, International Preliminary Report on Patentability mailed Jan. 4, 2024", 11 pgs.

"International Application Serial No. PCT/US2022/034359, International Preliminary Report on Patentability mailed Jan. 4, 2024", 12 pgs.

"International Application Serial No. PCT/US2022/034359, International Search Report mailed Sep. 30, 2022", 4 pgs.

"International Application Serial No. PCT/US2022/034359, Written Opinion mailed Sep. 30, 2022", 10 pgs.

Okuma, T, "Psychophysiological study on the depth of sleep in normal human subjects", Electroencephalography and Clinical Neurophysiology, Elsevier, NL, vol. 21, No. 2,, 8 pgs.

"U.S. Appl. No. 17/845,726, Non Final Office Action mailed Dec. 16, 2024", 47 pgs.

"U.S. Appl. No. 17/845,726, Response filed Nov. 4, 2024 to Restriction Requirement mailed Sep. 6, 2024", 9 pgs.

"Australian Application Serial No. 2022296509, Response filed Dec. 19, 2024 to First Examination Report mailed Sep. 25, 2024", 14 pgs.

"U.S. Appl. No. 17/845,726, Response filed Jan. 27, 2025 to Non Final Office Action mailed Dec. 16, 2024", 16 pgs.

"Australian Application Serial No. 2022296509, Second Examiners Report mailed Jan. 2, 2025", 3 pgs.

"Australian Application Serial No. 2022299056, Response filed Dec. 20, 2024 to First Examination Report mailed Sep. 30, 2024", 141 pgs.

"U.S. Appl. No. 17/845,726, Advisory Action mailed Jul. 17, 2025", 3 pgs.

"U.S. Appl. No. 17/845,726, Final Office Action mailed May 5, 2025", 41 pgs.

"U.S. Appl. No. 17/845,726, Response filed Jul. 1, 2025 to Final Office Action mailed May 5, 2025", 15 pgs.

"Australian Application Serial No. 2022296509, Response filed Aug. 15, 2025 to Second Examiners Report mailed Jan. 2, 2025", 10 pgs.

"U.S. Appl. No. 17/845,726, Examiner Interview Summary mailed Dec. 9, 2025", 3 pgs.

"U.S. Appl. No. 17/845,726, Non Final Office Action mailed Oct. 1, 2025", 40 pgs.

"U.S. Appl. No. 17/845,726, Response filed Dec. 10, 2025 to Non Final Office Action mailed Oct. 1, 2025", 14 pgs.

"Australian Application Serial No. 2022296509, Subsequent Examination Report mailed Sep. 8, 2025", 3 pgs.

* cited by examiner

CLOUD-BASED SENSOR OPERATION ADAPTED TO PATIENT BEHAVIOR

CLAIM OF PRIORITY

This application claims the benefit of U.S. Provisional Application No. 63/213,093, filed on Jun. 21, 2021, which is hereby incorporated by reference in its entirety.

TECHNICAL FIELD

This document relates generally to medical systems and more particularly to systems, devices, and methods for pain management.

BACKGROUND

Pain is one of the most common and among the most personally compelling reasons for seeking medical attention, and consumes considerable healthcare resources each year. The relation between etiology, underlying mechanisms and the specific symptoms and signs related to painful disorders is complex. Pain in an individual patient may be produced by more than one mechanism.

Chronic pain, such as pain present most of the time for a period of six months or longer during the prior year, is a highly pervasive complaint and consistently associated with psychological illness. Chronic pain may originate with a trauma, injury or infection, or there may be an ongoing cause of pain Chronic pain may also present in the absence of any past injury or evidence of body damage. Common chronic pain can include headache, low back pain, cancer pain, arthritis pain, neurogenic pain (pain resulting from damage to the peripheral nerves or to the central nervous system), or psychogenic pain (pain not due to past disease or injury or any visible sign of damage inside or outside the nervous system).

Chronic pain may be treated or alleviated using medications, acupuncture, surgery, and neuromodulation therapy such as local electrical stimulation or brain stimulation, among others. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), which can electrically stimulate tissue or nerve centers to treat nervous or muscular disorders. In an example, an IPG can deliver electrical pulses to a specific region in a patient's spinal cord, such as particular spinal nerve roots or nerve bundles, to create an analgesic effect that masks pain sensation.

SUMMARY

This document discusses systems, devices, and methods for remote monitoring and managing of patients with chronic pain. According to one example, a remote monitoring system comprises a cloud-computing device and a remote device. The cloud-computing device receives patient data including physiological or functional information sensed by sensors included in one or more holdable or wearable devices operable by the patient (e.g., mobile phones or smart wearables), or by sensors in an implantable device implanted in the patient, such as an implantable neuromodulation device for pain management. The cloud-computing device can provide on-demand cloud-based services, including establishing a correspondence between one or more physiological or functional states of the patient and one or more pain levels, detecting patient physiological or functional state, predicting a pain level for the physiological or functional state, and storing in a cloud storage the patient data and the predicted pain level, among other information. The cloud-based services can also include detecting a patient behavior using the received patient data, and generating a recommendation for adjusting sensor or device operations (e.g., operations of the sensors included in the mobile device or the smart wearable) based on the patient behavior. The remote device can access the cloud storage and the cloud-based services, provide the stored information to an authorized user or the patient, control the implantable device to initiate or adjust a neuromodulation therapy according to the predicted pain, or adjust sensor operations according to the recommendation.

According to one example, a remote monitoring system comprises one or more sensors to sense physiological or functional information from the patient, a cloud-computing device communicatively coupled to the one or more sensors, and a remote device. The cloud-computing device receives patient data including physiological or functional information, and provides on-demand cloud-based services including storing the received patient data in a cloud storage, detecting a patient behavior, and generating a sensor operation recommendation based on the detected patient behavior. The remote device can access the cloud storage and the cloud-based services, and adjust operations of the one or more sensors in accordance with the sensor operation recommendation.

Example 1 is a system for remote monitoring of a patient with an implantable device for pain management. The system comprises a cloud-computing device and a remote device. The cloud-computing device can be configured to receive patient data indicative of patient physiological or functional state, and to provide one or more cloud-based services including: establishing a correspondence between one or more physiological or functional states of the patient and one or more pain levels; detecting a physiological or functional state of the patient; predicting, for the detected physiological or functional state, a pain level using the established correspondence; and storing in a cloud storage one or more of the received patient data, the detected physiological or functional state, the established correspondence, or the predicted pain level. The remote device can be configured to access the cloud storage and the one or more cloud-based services via a communication network, and to provide the detected physiological or functional state or the predicted pain level to the patient or a user.

In Example 2, the subject matter of Example 1 optionally includes the remote device that can be configured to generate a control signal to the implantable device to initiate or adjust a neuromodulation therapy in accordance with the predicted pain level.

In Example 3, the subject matter of Example 2 optionally includes the neuromodulation therapy that can include a spinal cord stimulation therapy.

In Example 4, the subject matter of any one or more of Examples 1-3 optionally includes the received patient data that can include pain data and physical activity data, and the cloud-computing device that can be configured to: establish the correspondence including an activity-pain correlation between the pain data and the physical activity data; detect the physiological or functional state including a physical activity level; and predict the pain level corresponding to the detected physical activity level using the activity-pain correlation.

In Example 5, the subject matter of Example 4 optionally includes the remote device that can be configured to provide a recommendation to the patient to adjust physical activity based on the predicted pain level.

In Example 6, the subject matter of any one or more of Examples 4-5 optionally includes the cloud-computing device that can be configured to compare the detected activity level against an activity target, and the remote device that can be configured to provide a feedback on progression towards the activity target based on the comparison.

In Example 7, the subject matter of any one or more of Examples 4-6 optionally includes the cloud-computing device that can be configured to identify, from the activity-pain correlation, a first activity corresponding to worsened pain and a second activity corresponding to ameliorated pain; and the remote device is configured to provide the identified first and second activities to the patient or the user.

In Example 8, the subject matter of any one or more of Examples 4-7 optionally includes the cloud-computing device that can be configured to compute a pain score representing a pain level at a body location of the patient using the pain data, and to compute an activity score using the physical activity data; and the remote device that can be configured to display a first trend of the pain score over a time period and a second trend of the activity score over the same time period.

In Example 9, the subject matter of any one or more of Examples 1-8 optionally includes the one or more physiological or functional states that can include a sleep state and an awakening state, and the established correspondence is between the sleep and awakening states and corresponding pain levels, and wherein the cloud-computing device is configured to detect a sleep or awakening state of the patient using the received patient data, and to predict the pain level for the detected sleep or awakening state using the established correspondence.

In Example 10, the subject matter of Example 9 optionally includes the patient data that can include physiological or functional data collected from the patient by the implantable device or by a sensor in a wearable electronic device, and the cloud-computing device that can be configured to detect the sleep or awakening state using the physiological or functional data.

In Example 11, the subject matter of Example 10 optionally includes the physiological or functional data include one or more of a heart rate, a heart rate variability, or a blood oxygen saturation level.

In Example 12, the subject matter of any one or more of Examples 9-11 optionally includes the remote device that can be configured to provide an alert to the patient; and the cloud-computing device is configured to track patient reaction to the alert, and to detect the sleep or awakening state based on the tracked patient reaction to the alert.

In Example 13, the subject matter of Example 12 optionally includes the alert that can include textual, graphical, or vibrational alert.

In Example 14, the subject matter of any one or more of Examples 9-13 optionally includes the cloud-computing device that can configured to track patient interaction with a mobile device, and to detect the sleep or awakening state based on the tracked patient interaction with the mobile device.

In Example 15, the subject matter of any one or more of Examples 9-14 optionally includes the patient data that can include accelerometer data collected from the patient by an accelerometer in a mobile device, the accelerometer data indicative of patient motion when manipulating the mobile device, and the cloud-computing device that can be configured to detect the sleep or awakening state using the accelerometer data.

In Example 16, the subject matter of any one or more of Examples 9-15 optionally includes the cloud-computing device that can be configured to compute a sleep score indicative of a sleep quality using the received patient data, and to predict the pain level based on the sleep score.

In Example 17, the subject matter of any one or more of Examples 1-16 optionally includes the remote device that can include a mobile device operable by the patient and configured to collect the patient data.

In Example 18, the subject matter of Example 17 optionally includes the mobile device that can be configured to communicate with the implantable device, and to collect therefrom neuromodulation therapy data.

In Example 19, the subject matter of any one or more of Examples 17-18 optionally includes the mobile device that can include a user interface configured to receive patient reported outcome (PRO) including a patient input of pain or physical activity.

In Example 20, the subject matter of any one or more of Examples 17-19 optionally includes the mobile device that can be configured to communicate with a wearable electronic device comprising one or more sensors configured to collect from the patient physiological or functional data including one or more of: a physical activity signal; a posture; a sleep state or sleep stage; a photoplethysmography (PPG) signal; a cardiac electrical activity signal; a heart rate; a heart rate variability; a blood oxygen saturation level; a blood pressure; or a respiration signal.

In Example 21, the subject matter of any one or more of Examples 1-20 optionally includes the cloud-computing device that can be configured to determine an indicator of patient compliance with a data collection protocol using the received patient data, and the remote device that can be configured to provide a recommendation to adjust data collection based on the indicator of patient compliance.

In Example 22, the subject matter of Example 21 optionally includes the cloud-computing device that can be configured to select the patient to enroll in a clinical study based at least on the indicator of patient compliance.

Example 23 is a method for remote monitoring of a patient with an implantable device for pain management via a cloud-based system comprising a cloud-computing device. The method comprises steps including: collecting patient data indicative of patient physiological or functional state using the implantable device or one or more external devices; establishing a correspondence between one or more physiological or functional states of the patient and one or more pain levels; detecting a physiological or functional state of the patient; predicting, for the detected physiological or functional state, a corresponding pain level using the established correspondence; storing, in a cloud storage of the cloud-based system, one or more of the collected patient data, the detected physiological or functional state, the established correspondence, or the predicted pain level; and providing the detected physiological or functional state or the predicted pain level to the patient or a user.

In Example 24, the subject matter of Example 23 optionally includes initiating or adjusting a neuromodulation therapy in accordance with the predicted pain level.

In Example 25, the subject matter of any one or more of Examples 23-24 optionally includes the patient data that can include one or more of: physiological or functional data collected by one or more sensors; neuromodulation therapy data collected by the implantable device; or patient reported outcome (PRO) collected by a mobile device.

In Example 26, the subject matter of any one or more of Examples 23-25 optionally includes the patient data that can include pain data and physical activity data. The operation of establishing the correspondence can include establishing an activity-pain correlation between the pain data and the physical activity data; detecting the physiological or functional state includes detecting a physical activity level, and predicting the pain level includes a pain level corresponding to the detected physical activity level using the activity-pain correlation.

In Example 27, the subject matter of Example 26 optionally includes identifying, from the activity-pain correlation, a first activity corresponding to worsened pain and a second activity corresponding to ameliorated pain, and providing the identified first and second activities to the patient or the user.

In Example 28, the subject matter of any one or more of Examples 26-27 optionally include providing a recommendation to the patient to adjust physical activity based on the predicted pain level.

In Example 29, the subject matter of any one or more of Examples 26-28 optionally includes computing a pain score representing a pain level at a body location of the patient using the pain data, computing an activity score using the physical activity data, and displaying a first trend of the pain score over a time period and a second trend of activity score over the same time period.

In Example 30, the subject matter of any one or more of Examples 23-29 optionally include the one or more physiological or functional states that can include a sleep state and an awakening state. The operation of establishing the correspondence can include establishing a correspondence between the sleep and awakening states and corresponding pain levels, detecting the physiological or functional state includes detecting a sleep or awakening state of the patient, and predicting the pain level includes predicting a pain level for the detected sleep or awakening state using the established correspondence.

In Example 31, the subject matter of Example 30 optionally includes the patient data that can include sensor data collected by a sensor in the implantable device or by a sensor in a wearable electronic device. The detection of sleep or awakening state can include using the sensor data.

In Example 32, the subject matter of any one or more of Examples 30-31 optionally includes detecting the sleep or awakening state that can include providing an alert to the patient from a remote device, and tracking patient reaction to the alert.

In Example 33, the subject matter of any one or more of Examples 30-32 optionally includes detecting the sleep or awakening state that can include tracking patient interaction with a mobile device.

In Example 34, the subject matter of any one or more of Examples 33 optionally includes the patient data that can include accelerometer data indicative of patient motion when manipulating a mobile device. The detection of the sleep or awakening state can include using the accelerometer data.

In Example 35, the subject matter of any one or more of Examples 34 optionally include computing a sleep score indicative of a sleep quality using the patient data, and predicting the pain level based on the sleep score.

In Example 36, the subject matter of any one or more of Examples 23-35 optionally includes determining an indicator of patient compliance with a data collection protocol using the patient data, and providing a recommendation to the patient or the user to adjust data collection based on the indicator of patient compliance.

In Example 37, the subject matter of Example 36 optionally includes selecting the patient to enroll in a clinical study based at least on the indicator of patient compliance.

Example 38 is a non-transitory machine-readable storage medium that includes instructions that, when executed by one or more processors of a machine, cause the machine to perform operations comprising: receiving patient data collected from a patient by an implantable device implanted in the patient or one or more external devices, the patient data indicative of patient physiological or functional state; establishing a correspondence between one or more physiological or functional states and one or more pain levels; detecting a physiological or functional state of the patient; predicting, for the detected physiological or functional state, a corresponding pain level using the established correspondence; storing, in a cloud storage of a cloud-based system, one or more of the received patient data, the detected physiological or functional state, the established correspondence, or the predicted pain level; and providing the detected physiological or functional state or the predicted pain level to the patient or a user.

In Example 39, the subject matter of Example 38 optionally includes the received patient data that can include pain data and physical activity data. The operation of establishing the correspondence can include establishing an activity-pain correlation between the pain data and the physical activity data. The operation of detecting the physiological or functional state can include detecting a physical activity level. The operation predicting the pain level can include predicting a pain level for the detected physical activity level using the activity-pain correlation.

In Example 40, the subject matter of any one or more of Examples 38-39 optionally include the one or more physiological or functional states that can include a sleep state and an awakening state. The operation of establishing the correspondence can include a correspondence between the sleep and awakening states and corresponding pain levels. The operation of detecting the physiological or functional state can include detecting a sleep or awakening state of the patient. The operation of predicting the pain level can include predicting a pain level for the detected sleep or awakening state using the established correspondence.

Example 41 is a system for remote monitoring of a patient with an implantable device for pain management. The system comprises one or more sensors configured to sense physiological or functional information from the patient, a cloud-computing device communicatively coupled to the one or more sensors, and a remote device. The cloud-computing device can be configured to receive patient data including the sensed physiological or function information, and to provide one or more cloud-based services including: storing the received patient data in a cloud storage; detecting a patient behavior using the received patient data; and generating a sensor operation recommendation based on the detected patient behavior. The remote device configured to access the cloud storage and the one or more cloud-based services via a communication network, and to adjust operations of the one or more sensors in accordance with the sensor operation recommendation.

In Example 42, the subject matter of Example 41 optionally includes the one or more cloud-based services that can further include predicting a pain level using the received patient data, and that the remote device can be configured to generate a control signal to the implantable device to initiate or adjust a neuromodulation therapy for pain management in accordance with the predicted pain.

In Example 43, the subject matter of Example 42 optionally includes the neuromodulation therapy that can include a spinal cord stimulation therapy.

In Example 44, the subject matter of any one or more of Examples 41-43 optionally includes the cloud-computing device that can be configured to: detect the patient behavior including detecting a sleep state or receiving a sleep schedule from the patient, and generate the sensor operation recommendation based on the sleep state or the sleep schedule.

In Example 45, the subject matter of any one or more of Examples 41-44 optionally includes the cloud-computing device that can be configured to detect the patient behavior including detecting a physical activity level or receiving a physical activity schedule from the patient, and generate the sensor operation recommendation based on the physical activity level or the physical activity schedule.

In Example 46, the subject matter of any one or more of Examples 41-45 optionally includes the one or more sensors that can be powered by a rechargeable battery in the implantable device or in a mobile device, and the cloud-computing device that can be configured to generate the sensor operation recommendation including a recommendation to charge the rechargeable battery based on the detected patient behavior.

In Example 47, the subject matter of Example 46 optionally includes the cloud-computing device that can be configured to generate the sensor operation recommendation further based on a battery level of the rechargeable battery.

In Example 48, the subject matter of any one or more of Examples 46-47 optionally includes the cloud-computing device that can further be configured to generate a sensor-usage trend over time for at least one of the one or more sensors, and to generate the recommendation to charge the rechargeable battery further based on the sensor-usage trend.

In Example 49, the subject matter of any one or more of Examples 41-48 optionally includes the cloud-computing device that can be configured to generate the sensor operation recommendation including a recommendation to activate or deactivate the one or more sensors based on the detected patient behavior.

In Example 50, the subject matter of any one or more of Examples 41-49 optionally includes the cloud-computing device that can be configured to generate the sensor operation recommendation including a recommendation to adjust a data acquisition schedule for the one or more sensors based on the detected patient behavior.

In Example 51, the subject matter of any one or more of Examples 41-50 optionally includes the cloud-computing device that can be configured to generate the sensor operation recommendation including a recommendation to adjust a data sampling rate for the one or more sensors.

In Example 52, the subject matter of any one or more of Examples 41-51 optionally includes the cloud-computing device that can be further configured to: detect a sensor anomaly using the sensed physiological or function information, the sensor anomaly indicating a misplacement of the one or more sensors on the patient; and provide an indication of the detected sensor anomaly to the patient or a user.

In Example 53, the subject matter of Example 52 optionally includes the one or more sensors included in a wearable electronic device. The sensor anomaly can indicate an improper wearing of the wearable electronic device on the patient. The cloud-computing device can be configured to generate the sensor operation recommendation including a recommendation to adjust the wearing of the wearable electronic device.

In Example 54, the subject matter of any one or more of Examples 52-53 optionally includes the cloud-computing device that can be configured to compute a sensor data quality score using the sensed physiological or function information, and to detect the sensor anomaly based on the sensor data quality scor.

In Example 55, the subject matter of any one or more of Examples 52-54 optionally includes the one or more sensors that can include a first sensor and a different second sensor, and the cloud-computing device that can be configured to: detect the sensor anomaly using physiological or function information sensed by the first sensor; and validate the detected sensor anomaly using physiological or function information sensed by the second sensor.

In Example 56, the subject matter of any one or more of Examples 52-55 optionally includes the cloud-computing device that can be configured to receive an input from the patient or the user to confirm the sensor anomaly detected using the sensed physiological or function information, and to provide an indication of the confirmed sensor anomaly to the patient or the user.

In Example 57, the subject matter of any one or more of Examples 41-56 optionally includes the remote device that can include a mobile device operable by the patient and configured to collect the patient data.

In Example 58, the subject matter of Example 57 optionally includes the mobile device that can be configured to communicate with the implantable device, and to collect therefrom neuromodulation therapy data for pain management.

In Example 59, the subject matter of any one or more of Examples 57-58 optionally includes the mobile device that can include a user interface configured to receive patient reported outcome (PRO) provided by the patient.

In Example 60, the subject matter of any one or more of Examples 57-59 optionally includes the mobile device that can be configured to communicate with a wearable electronic device comprising one or more sensors configured to collect physiological or functional data from the patient.

Example 61 is a method for remote monitoring of a patient with an implantable device for pain management via a cloud-based system comprising a cloud-computing device. The method comprises steps including: receiving patient data including physiological or function information sensed by one or more sensors included in the implantable device or in one or more external devices; detecting patient behavior using the received patient data; generating a sensor operation recommendation based on the detected patient behavior; and adjusting operations of the one or more sensors in accordance with the sensor operation recommendation.

In Example 62, the subject matter of Example 61 optionally includes predicting a pain level using the received patient data, and initiating or adjusting a neuromodulation therapy in accordance with the predicted pain level.

In Example 63, the subject matter of any one or more of Examples 61-62 optionally includes the patient data that can include one or more of physiological or functional data collected by one or more sensors; neuromodulation therapy data collected by the implantable device; or patient reported outcome (PRO) collected by a mobile device.

In Example 64, the subject matter of any one or more of Examples 61-63 optionally includes detecting the patient behavior includes detecting a sleep state or receiving a sleep schedule from the patient, and generating the sensor operation recommendation is based on the sleep state or the sleep schedule.

In Example 65, the subject matter of any one or more of Examples 61-64 optionally includes detecting the patient behavior includes detecting a physical activity level or receiving a physical activity schedule from the patient, and generating the sensor operation recommendation is based on the physical activity level or the physical activity schedule.

In Example 66, the subject matter of any one or more of Examples 61-65 optionally includes generating the sensor operation recommendation includes generating a recommendation to charge a rechargeable battery based on the detected patient behavior, the rechargeable battery powering the one or more sensors.

In Example 67, the subject matter of Example 66 optionally includes generating the sensor operation recommendation that can be further based on a battery level of the rechargeable battery.

In Example 68, the subject matter of any one or more of Examples 66-67 optionally includes generating a sensor-usage trend over time for at least one of the one or more sensors, and wherein generating the recommendation to charge the rechargeable battery can be further based on the sensor-usage trend.

In Example 69, the subject matter of any one or more of Examples 61-68 optionally includes generating the sensor operation recommendation includes one or more of recommendations of, based on the detected patient behavior, activating or deactivating the one or more sensors adjusting a data acquisition schedule for the one or more sensors, or adjusting a data sampling rate for the one or more sensors.

In Example 70, the subject matter of any one or more of Examples 61-69 optionally includes detecting a sensor anomaly using the sensed physiological or function information, the sensor anomaly indicating a misplacement of the one or more sensors on the patient, and providing an indication of the detected sensor anomaly to the patient or a user.

In Example 71, the subject matter of Example 70 optionally includes detecting the sensor anomaly that indicate detecting an improper wearing of a wearable electronic device on the patient, and generating the sensor operation recommendation that can include a recommendation to adjust the wearing of the wearable electronic device.

In Example 72, the subject matter of any one or more of Examples 70-71 optionally includes the one or more sensors that can include a first sensor and a different second sensor. The detecting the sensor anomaly can include detecting the sensor anomaly using first physiological or function information sensed by the first sensor. The validating the detected sensor anomaly can include using second physiological or function information sensed by the second sensor.

In Example 73, the subject matter of any one or more of Examples 70-72 optionally includes receiving an input from the patient or the user to confirm the sensor anomaly detected using the sensed physiological or function information, and providing an indication of the confirmed sensor anomaly to the patient or the user.

Example 74 is a non-transitory machine-readable storage medium that includes instructions that, when executed by one or more processors of a machine, cause the machine to perform operations comprising: receiving patient data collected from a patient including physiological or function information sensed by one or more sensors included in an implantable device or in one or more external devices; detecting patient behavior using the received patient data; generating a sensor operation recommendation based on the detected patient behavior; and adjusting operations of the one or more sensors in accordance with the sensor operation recommendation.

In Example 75, the subject matter of Example 74 optionally includes the instructions causing the machine to perform operations including: predicting a pain level using the received patient data; and initiating or adjusting a neuromodulation therapy in accordance with the predicted pain level.

In Example 76, the subject matter of any one or more of Examples 74-75 optionally includes the operation of generating the sensor operation recommendation that can include one or more of recommendations of, based on the detected patient behavior: charging a rechargeable battery that powers the one or more sensors; activating or deactivating the one or more sensors; adjusting a data acquisition schedule for the one or more sensors; or adjusting a data sampling rate for the one or more sensors.

In Example 77, the subject matter of any one or more of Examples 74-76 optionally includes the instructions causing the machine to perform operations including: detecting a sensor anomaly using the sensed physiological or function information, the sensor anomaly indicating a misplacement of the one or more sensors on the patient; and providing an indication of the detected sensor anomaly to the patient or a user.

In Example 78, the subject matter of Example 77 optionally includes the instructions causing the machine to perform operations including validating the detected sensor anomaly using physiological or function information sensed by a sensor or an input received from the patient or the user.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
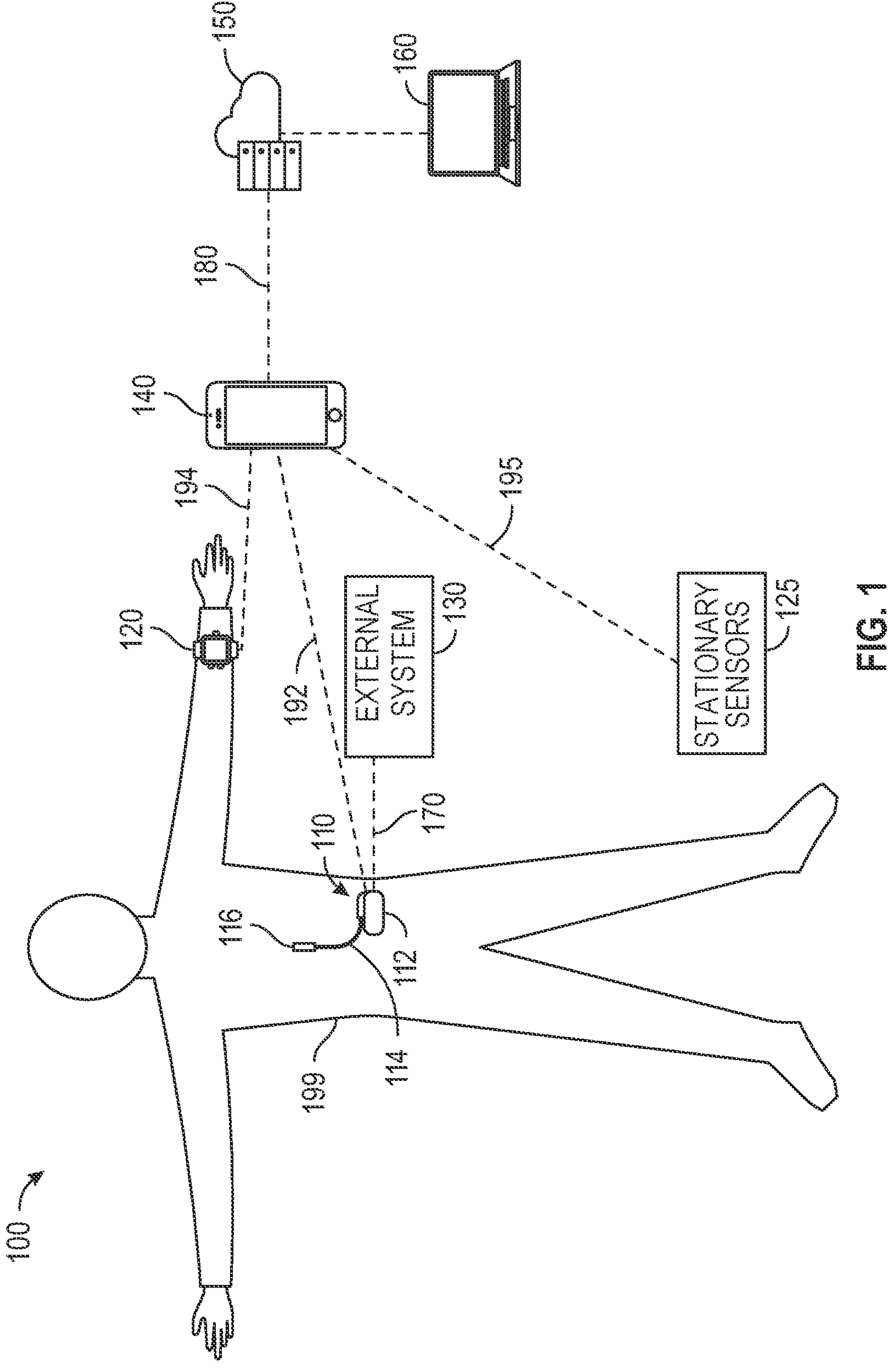
FIG. 1 illustrates generally an example of a cloud-based patient monitoring and pain management system 100 and portions of an environment in which the system 100 may operate.

By way of example, chronic pain management may involve monitoring patient pain symptoms and physical and emotional well-being, determining appropriate treatment options (e.g., neuromodulation therapies with an implantable device), and evaluating patient response to therapy. Effective monitoring and accurate pain evaluation are important for managing patients with chronic pain. For patients with an implantable neuromodulation device for pain control, patient monitoring and pain assessment are typically performed in a clinic or other medical facilities. However, for some patients and on some occasions, in-person patient monitoring and pain management in a clinical setting may not always be feasible or practical. For example, some patients with chronic pain and under long-term treatment (e.g., via an implantable neuromodulator) may experience gradual physiological or emotional changes, which can get unnoticed for an extended period of time when the patient is outside a clinical setting until it becomes symptomatic and get managed during a clinic visit. Continuous or periodic monitoring of such patients would be desirable to timely detect pain progression and changes in patient health. On the other hand, some chronic-pain patients may experience sudden change in their pain sensation, and require immediate pain assessment, a therapy titration, or neuromodulation device check. However, geographic barriers to medical facilities and resources may prevent or delay the clinical evaluation and treatment titration. Additionally, certain extraordinary circumstances like pandemic or lockdown may make it inconvenient, if not impossible, to access to a medical facility.

The present inventors have recognized that a remotely-accessible patient monitoring and pain management platform can be more desirable and advantageous in certain situations than a conventional in-person visit at a clinic. Such a patient monitoring and pain management platform can be implanted to enable efficient monitoring of patient health status (including chronic pain) and responses to pain therapy, and configure their neuromodulation devices such as adjusting an electrostimulation setting for pain therapy with minimal or no direct intervention from others. Such a remotely-accessible pain management system may be empowered by advanced cloud-computing and networking technologies to provide improved pain management functionality and user experience. For example, using cloud-based services, clinicians can perform remote patient monitoring and pain management continuously, periodically, or at any desired time between clinic visits.

Disclosed herein are systems, devices, and methods for remote monitoring and managing of patients with chronic pain. A remote monitoring system comprises a cloud-computing device and a remote device. The cloud-computing device receives patient data including physiological or functional information sensed by sensors, therapy data, and patient reported outcome (PRO), and provides on-demand cloud-based services. The cloud-based service include establishing a correspondence between one or more physiological or functional states of the patient and one or more pain levels, detecting patient physiological or functional state, predicting a pain level for the physiological or functional state, and storing in a cloud storage the patient data and the predicted pain level, among other information. The cloud-based services can include detecting a patient behavior and generating recommendation for adjusting sensor operations based on the patient behavior. The remote device can access the cloud storage and the cloud-based services, provide the stored information to an authorized user or the patient, control an implantable device to initiate or adjust a neuromodulation therapy for pain management according to the predicted pain, or adjust sensor operations.

The cloud-based remote patient monitoring and pain management system and methods of using the same, as described in this document, may improve the technology of device-based pain assessment and therapy. According to one aspect of the present subject matter, a remote patient monitoring and pain management platform can be implemented in and executed by a personal mobile device, such as a smartphone. The remote patient monitoring and pain management platform interconnects the patient and human assistants (e.g., a clinician, a caregiver, or a device expert such as a device manufacturer representative) by networked hardware and services, and enables multi-party information exchange regarding pain perception, pain therapy, and device integrity testing or trouble-shooting, among other capabilities. The remote patient monitoring and pain management platform as described herein helps overcome geographic barriers to medical facilities and resources, which can be particularly beneficial for patients in medically underserved communities or during extraordinary public-health or social crisis such as a pandemic or lockdown. The remote patient monitoring and pain management platform may incorporate advanced computing and networking technologies to provide improved pain management functionality and user experience. The remote patient monitoring and pain management platform may respond to patient inquires more quickly and more consistently, thereby increasing the efficiency of pain management and care delivery and improving user experience. With convenient user control and remote access by one or more human assistants, safety, reliability, and efficacy of individualized pain management can be maintained or improved. Timely delivery of individualized pain therapies may improve patient outcome, enhance battery longevity of an implantable neuromodulation device, and reduce clinic visits or hospitalization. The remote patient monitoring and pain management platform may also help reduce human professionals' in-person interaction with patients yet without impairing the quality of patient care, and allow them to focus on complex tasks that require more skills and critical thinking. Accordingly, the overall healthcare cost may be reduced.

The present system can be implemented using a combination of hardware and software designed to provide a pain management regimen to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, among others. The remote patient monitoring and pain management system may provide recommendations to the patient or a clinician regarding pain treatment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

FIG. 1 illustrates, by way of example and not limitation, an example of a cloud-based patient monitoring and pain management system 100 and portions of an environment in which the system 100 may operate. The system 100 may be used to monitor a patient having an ambulatory device, such as an implantable neuromodulator for managing chronic pain. The implantable neuromodulator can deliver stimulation pulses or other energy modalities to modulate the spinal cord or other neural targets.

The cloud-based patient monitoring and pain management system 100 may include one or more of an implantable system 110 for implantation in the body 199 of the patient, a wearable electronic device 120 to be worn on the patient body 199 (such as on a wrist or an arm as shown), an external system 130, a mobile device 140 operable by a patient, a cloud-computing device 150, and one or more user terminals 160. The implantable system 110 may include an ambulatory medical device (AMD), such as an implantable pulse generator (IPG) 112, a lead system 114, and one or more electrodes 116. The IPG 112 may be configured for subcutaneous implant in a patient's chest, abdomen, or other parts of the body 199. The IPG 112 may include a hermetically sealed housing that houses sensing circuitry to sense physiological or functional signals from the patient via sensing electrodes or ambulatory sensors associated with the patient and in communication with the IPG 112. In some examples, the sensing electrodes or the ambulatory sensors may be included within the IPG 112. Physiological or functional signals may be sensed during a pain episode. The sensed physiological or functional signals may include at least one signal indicative of muscle electrical or mechanical activity at a specific body location. The IPG 112 may generate signal metrics indicative of muscle tension from the sensed muscle electrical or mechanical activity signal, and characterize and quantify the pain, such as to determine onset, intensity, severity, duration, or patterns of the pain experienced by the subject. The IPG 112 may generate an alert to indicate occurrence of a pain episode, pain exacerbation, or efficacy of pain therapy, and present the alert to a clinician.

The IPG 112 may provide neuromodulation therapy to the patient, such as therapies for treating or alleviating pain. The IPG 112 may generate electrical, magnetic, or other types of energy. In some examples, in addition or alternative to the IPG 112, a drug delivery system such as a drug infusion pump can be included to deliver pain medication to the patient, such as morphine sulfate or ziconotide, among others.

The IPG 112 may include electrostimulation circuitry that generates electrostimulation pulses to stimulate a neural target via the electrodes 116 operably connected to the IPG 112. In an example, the electrodes 116 may be positioned on or near a port of the spinal cord of the patient, and the electrostimulation circuitry may be configured to deliver SCS to alter or alleviate pain. In another example, the electrodes 116 may be surgically placed at other neural targets such as a brain or a peripheral neutral tissue, and the electrostimulation circuitry may be configured to deliver brain or peripheral stimulations. Examples of electrostimulation may include deep brain stimulation (DBS), trigeminal nerve stimulation, occipital nerve stimulation, vagus nerve stimulation (VNS), sacral nerve stimulation, sphenopalatine ganglion stimulation, sympathetic nerve modulation, adrenal gland modulation, baroreceptor stimulation, or transcranial magnetic stimulation, spinal cord stimulation (SCS), dorsal root ganglia (DRG) stimulation, motor cortex stimulation (MCS), transcranial direct current stimulation (tDCS), transcutaneous spinal direct current stimulation (tsDCS), pudendal nerve stimulation, multifidus muscle stimulation, transcutaneous electrical nerve stimulation (TENS), tibial nerve stimulation, among other peripheral nerve or organ stimulation. The IPG 112 may additionally or alternatively provide therapies such as radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, other peripheral tissue denervation therapies, or nerve blocks or injections.

In various examples, the electrodes 116 may be disposed on one or more leads of the lead system 114 electrically coupled to the IPG 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IPG 112 and tissue of the patient. The neurostimulation pulses are each delivered from the IPG 112 through a set of electrodes selected from the electrodes 116. In various examples, the neurostimulation pulses may include one or more individually defined pulses, and the set of electrodes may be individually definable by the user for each of the individually defined pulses.

Although the discussion herein with regard to pain management is focused on implantable devices such as the IPG 112, this is meant only by way of example and not limitation. The cloud-based patient monitoring and pain management techniques discussed herein may also be applied to pain management via non-implantable devices, such as subcutaneous devices, wearable devices (e.g., wrist watch, patches, ring, necklace, garment- or shoe-mounted device, etc.), or other external medical devices, or a combination of implantable, wearable, or other external devices. The therapy, such as electrostimulation or medical therapies, may be used to treat various neurological disorders other than pain including, for example, epilepsy, obsessive compulsive disorder, tremor, Parkinson's disease, or dystonia, among other movement and affective disorders.

The external system 130 can be communicatively coupled to the IPG 112 via a communication link 170. The external system 130 may include a dedicated hardware/software system such as a programmer, a remote server-based patient management system, or alternatively a system defined predominantly by software running on a standard personal computer. The external system 130 may be configured to control the operation of the IPG 112, such as to program the IPG 112 for delivering neuromodulation therapy. The external system 130 may additionally receive via the communication link 170 information acquired by IPG 112, such as one or more sensor signals. In an example, a user may use the external system 130 to program the IPG 112 to deliver pain therapy in a closed-loop fashion based on the signals received from the IPG 112. The external system 130 may include a display that can display information including, for example, signal received by the IPG 112, a pain or paresthesia map indicating pain or paresthesia perception at various body locations of the patient, programming of pain therapy such as a stimulation setting including parameters and their values, among others. In some examples, the external system 130 may generate an alert notification. The alert notifications may include a Web page update, phone or pager call. E-mail, SMS, text or "Instant" message, as well as a message to the patient and a simultaneous direct notification to emergency services and to the clinician. Other alert notifications are possible.

The communication link 170 may include one or more communication channels and intermediate devices between the external system and the IPG 112. In an example, the communication link 170 may be a wired connection. In another example, the communication link 170 may be a wireless link, such as an inductive telemetry link, a capacitive telemetry link, a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible. In an example where the external system 130 includes a remote server such as configured as a uni-, multi- or distributed computing and processing system, the communication link 170 may be based on the Transmission Control Protocol/Internet Protocol (TCP/IP) network communication specification, although other types or combinations of networking implementations are possible. Similarly, other network topologies and arrangements are possible.

The communication link 170 may provide for data transmission between the IPG 112 and the external system 130. The transmitted data may include, for example, real-time sensor signals acquired by and stored in the IPG 112, therapy history data, data indicating device operational status of the IPG 112, one or more programming instructions to the IPG 112 which may include configurations for sensing physiologic signal or stimulation commands and stimulation parameters, or device self-diagnostic test, among others. In some examples, the IPG 112 may be coupled to the external system 130 further via an intermediate control device, such as a handheld external remote control device to remotely instruct the IPG 112 to generate electrical stimulation pulses in accordance with selected stimulation parameters produced by the external system 130.

The wearable electronic device 120 can include a smart watch, a smart wristband, or a smart ring, among other smart wearables. The wearable electronic device 120 can include, or be associated with, one or more sensors to sense physiological or functional information from the patient. Examples of the physiological information may include cardiac electrical activity, electrocardiograms (ECGs), heart rate, heart rate variability (HRV), a photoplethysmography (PPG) signal, blood oxygen saturation (SpO2) such as derived from the PPG signal, blood pressure, a respiration signal, respiratory rate, tidal volume, galvanic skin response, maximum rate of oxygen consumption ($VO2_{max}$) during exercise, peripheral body temperatures, among others. Examples of the functional information may include motor activities such as posture, gait, balance, or physical activities, among others. The functional information may also include sleep or awakening state. Chronic pain patients may experience frequent disrupted sleep or change of sleep patterns. The functional information may be sensed using one or more motions sensors, such as an accelerometer, a gyroscope (which may be a one-, two-, or three-axis gyroscope), a magnetometer (e.g., a compass), an inclinometer, a goniometer, an electromagnetic tracking system (ETS), or a global positioning system (GPS) sensor, among others. In some examples, the motion sensors may detect frequency or duration of sleep position switch, sleep incline, or other indicators of sleep quality.

The wearable electronic device 120 can include a processor to execute a software application (a wearable "app") to collect physiological and functional information from the patient, and process such information to generate one or more physiological or functional parameters. In an example, the wearable electronic device 120 can access to on-demand cloud-based services in the cloud-computing device 150, and process the collected physiological and functional information using the cloud-based services. The wearable app on the wearable electronic device 120 can display the collected or processed physiological and functional information on a user interface, and receive patient input from a user interface.

The wearable electronic device 120 can be communicatively coupled to the mobile device 140 via the a short-range communication link 194, such as ZigBee, or Bluetooth, among other wireless communication modes. The physiological and functional information received and processed by the wearable electronic device 120 can be transmitted to the mobile device 140. The mobile device 140 can be a personal mobile electronic device operable by the patient, such as a smart phone, a tablet, or a laptop computer, among other mobile computing devices. The mobile device 140 can execute a software application (a mobile "app") acting as a huh for patient data collection from various sources. For example, physiological and functional information collected and processed by the wearable electronic device 120 can be provided to the mobile device 140 via the short-range communication link 194. Data collected and processed by the IPG 112, including the physiological or functional data, device usage and diagnostic data, and therapy data (e.g., neuromodulation therapy such as SCS for pain relief), can be provided to the mobile device 140 via a short-range communication link 192, such as ZigBee, or Bluetooth, among other wireless communication modes.

The mobile app on the mobile device 140 can receive patient reported outcome (PRO). The PRO can include patient response to a questionnaire. Various questionnaires may be provided to the patient, such as displayed on a user interface of the mobile device 140. The patient response to such questionnaires may be valuable to the clinicians managing the patient. In an example, the mobile device 140 can present to the patient a questionnaire on pain sensation. The mobile app can receive patient description or pain or paresthesia sensation (e.g., intensity, severity, duration, body location, or pattern of pain or paresthesia). In an example, the PRO of pain sensation may include the patient's quantitative rating of pain level on a numerical scale (e.g., 0-10). In some examples, the PRO may include a pain drawing including the patient's depiction or identification of pain locations on the body and optionally pain quality description, or a paresthesia drawing including patient depiction or identification of body locations where paresthesia from stimulation is felt, and optionally paresthesia quality description. In some examples, the PRO may include questionnaires about patient general health status, physical functions such as physical activities, sleep qualities, mood or mental health status, among others. In some examples, the PRO may include a patient report on their compliance with a daily routine or a clinical protocol.

In some examples, a questionnaire may additionally or alternatively be presented on the wearable electronic device 120, such as a smart watch. The wearable electronic device 120 can execute a wearable app to receive PRO, such as patient response to the questionnaire, via the user interface of the smart watch. For example, the patient may use the smart watch bezel to select and control a user-interface control element, and respond to the questionnaire. The patient may use the smart watch bezel to rotate a pain drawing at different viewing perspectives and displaying different body locations. In another example, the patient may use the smart watch bezel to select colors, or adjust one or more color properties (e.g., saturation, tone, brightness, or hue) to distinguish different pain levels or at different body locations on a pain drawing.

The PRO can be provided in various formats including, for example, textual, graphical, audio, video, among other or a mixture of formats. The mobile app on the mobile device 140, or the wearable app on the wearable electronic device 120, can interpret the PRO, and extract information such as patient subjective pain experience or feedback on pain therapy (e.g., pain characteristics extracted from the pain drawing), and communicate such information to the cloud-computing device 150.

The mobile device 140 may include a communication module, such as a transceiver circuit, to establish data communication with the cloud-computing device 150. The mobile device 140 can securely route the data received from different sources (e.g., the IPG 112, the wearable electronic device 120, or the mobile device 140) to the cloud-computing device 150 via a communication link 180.

In some examples, physiological and functional information may be collected from the patient using one or more stationary sensors 125 in an environment of patient's daily life such as at a bedside, in a room at patient home, or in a testing room at a clinic or medical facility. In an example, a motion sensor may be mounted on a chair, a bed (e.g., under or attached to a mattress), or a fixture in a patient's environment. Unlike the wearable sensors which are ambulatory in nature, the stationary sensors 125 can detect one or more functional signals when the patient enters, or remains within, an environment within the scope of surveillance of the stationary sensors 125. Examples of the stationary sensors 125 may include a camera or a video recorder configured to capture an image, an image sequence, or a video of the patient at a specific physical state, such as sitting, standing, walking, or doing physical activities. In an example, the camera may be an infrared camera. In an example, the camera is a digital camera that may generate digital data representation of an image or a video sequence. Functional parameters such as patient posture, gait, balance, and range of motion can be generated from the image data image.

In an example, the stationary sensors 125 can include a weight sensor in a smart scale that can measure body weight of the patient. Chronic pain and obesity are common comorbidities. Reducing body weight may help reduce chronic pain levels. Monitoring patient body weight can be beneficial for managing chronic pain in a patient. In some examples, the stationary sensors 125 can measure or estimate body compositions including, for example, body fat percentage, body mass index (BMT), among others. Body fat percentage can be correlated to pain levels. A higher body fat levels could lead to deconditioning of pain pathways. Reliable body fat measurement at home can provide value to a monitoring physician, particularly if they are advising their patient to make necessary lifestyle changes to reduce weight. In an example, a body fat sensor can be an be incorporated into a smart scale. The smart scale includes an excitation signal generator that can sense electrical pulses towards the body. The body fat sensor can measure a responsive or reflected signal, and estimate a body fat percentage based at least on a relative change in electrical pulse strength.

The stationary sensors 125 can include or be associated with circuitry configured to communicate with the mobile device 140 via a short-range communication link 195, such as Wi-Fi, ZigBee, or Bluetooth, among other wireless communication modes. Measurements collected by the stationary sensors 125 (e.g., body weight or body fat percentage) can be transmitted to the mobile device 140 via the short-range communication link 195, and further be routed to the cloud-computing device 150 via the communication link 180.

The cloud-computing device 150, also referred to simply as a "cloud", can include a cloud server or a plurality of networked devices. The cloud-computing device 150 can include a cloud storge that can store data transmitted from networked devices such as the mobile device 140, and optionally the external system 130. The cloud-computing device 150 may include a suite of services (e.g., software as a service, platform as a service, infrastructure as a service) allowing for secured, on-demand access by multiple clients (or "tenants"), such as the wearable electronic device 120, the external system 130, the mobile device 140, or one or more user terminals 160. The user terminal 160 can be operated by authorized users from different locations, such as clinicians, medical professionals, or device manufacturer representatives. In an example, the user terminal 160 may include a timer to count the time a user spends accessing the cloud-based services to review and analyze the patient data. The time spent may be used for reimbursement for remote patient monitoring and pain management. In an example, the time spent, optionally a reimbursement threshold (e.g., every 20 minutes), may be displayed on a display of the user terminal 160.

The cloud-based services may include data analysis services for analyzing data received from various sources (e.g., devices or user input), establishing a correspondence between one or more physiological or functional states and one or more pain levels, detecting a physiological or functional state of the patient, detecting or predicting a pain level for the detected patient physiological or functional state using the established correspondence, storing data in the cloud storage, making recommendations to the patient (e.g., making behavior changes to promote pain relief), or making therapy recommendations to the health care provider (e.g., adjusting neuromodulation device setting), performing regular or scheduled device integrity testing or trouble-shooting, making or recommending adjustment to device operations with regard to data acquisition, or formatting and presenting data such as on a display. For example, the patient may use the mobile app on the mobile device 140 to securely access the cloud storage to review the stored data, or to access one or more cloud-based services to aggregate and process patient physiological or functional data and review the data. An authorized user (e.g., a clinician) may use an application installed on one of the user terminals 160 to securely access one or more cloud-based services to review the data, and to modify a device parameter for the IPG 112 such as to adjust pain therapy. Examples of the cloud-based services are discussed below such as with reference to FIGS. 3-8.

Portions of the cloud-based patient monitoring and pain management system 100 may be implemented using hardware, software, firmware, or combinations thereof. For example, portions of the IPG 112 or portions of the cloud-computing device 150 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
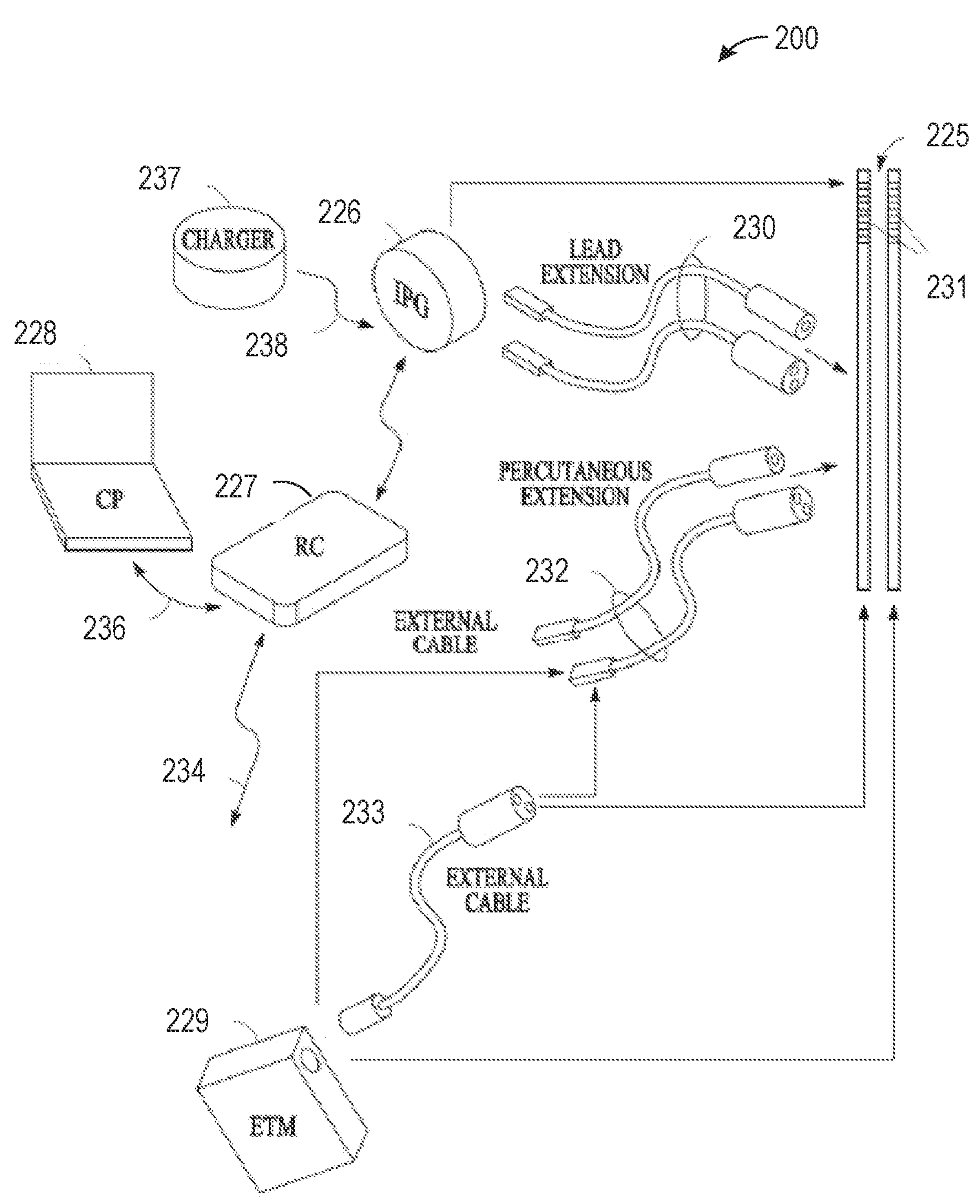
FIG. 2 illustrates generally an example of a Spinal Cord Stimulation (SCS) system.

FIG. 2 illustrates, by way of example, an example of a Spinal Cord Stimulation (SCS) system 200, also referred to as a Spinal Cord Neuromodulation system, which is an example of the implantable system 110. The SCS system 200 can include a plurality (illustrated as two) of implantable neuromodulation leads 225, an implantable pulse generator (IPG) 226, an external RC 227, a clinician's programmer (CP) 228, and an external trial modulator (ETM) 229. The IPG 226 may be physically connected via one or more percutaneous lead extensions 230 to the neuromodulation leads 225, which carry a plurality of electrodes 231. As illustrated, the neuromodulation leads 225 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 226 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 229 may also be physically connected via the percutaneous lead extensions 232 and external cable 233 to the neuromodulation leads 225. The ETM 229 may have similar pulse generation circuitry as the IPG 226 to deliver electrical neuromodulation energy to the electrodes in accordance with a set of neuromodulation parameters. The ETM 229 is a non-implantable device that is used on a trial basis after the neuromodulation leads 225 have been implanted and prior to implantation of the IPG 226, to test the responsiveness of the neuromodulation that is to be provided. Functions described herein with respect to the IPG 226 can likewise be performed with respect to the ETM 229.

The RC 227 may be used to telemetrically control the ETM 229 via a bi-directional RF communications link 234. The RC 227 may be used to telemetrically control the IPG 226 via a bi-directional RF communications link 235. Such control allows the IPG 226 to be turned on or off and to be programmed with different neuromodulation parameter sets. The IPG 226 may also be operated to modify the programmed neuromodulation parameters to actively control the characteristics of the electrical neuromodulation energy output by the IPG 226. A clinician may use the CP 228 to program neuromodulation parameters into the IPG 226 and ETM 229 in the operating room and in follow-up sessions.

The CP 228 may indirectly communicate with the IPG 226 or ETM 229, through the RC 227, via an IR communications link 236 or another link. The CP 228 may directly communicate with the IPG 226 or ETM 229 via an RF communications link or other link (not shown). The clinician detailed neuromodulation parameters provided by the CP 228 may also be used to program the RC 227, so that the neuromodulation parameters can be subsequently modified by operation of the RC 227 in a stand-alone mode (i.e., without the assistance of the CP 228). Various devices may function as the CP 228. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 228. Alternatively, such programming methodologies can be performed using firmware or hardware. In any event, the CP 228 may actively control the characteristics of the electrical neuromodulation generated by the IPG 226 to allow the desired parameters to be determined based on patient feedback or other feedback and for subsequently programming the IPG 226 with the desired neuromodulation parameters. To allow the user to perform these functions, the CP 228 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in a surgical or clinical setting.

An external charger 237 may be a portable device used to transcutaneously charge the IPG via a wireless link such as an inductive link 238. Once the IPG has been programmed, and its power source has been charged by the external charger or otherwise replenished, the IPG may function as programmed without the RC or CP being present.

Figure 3:
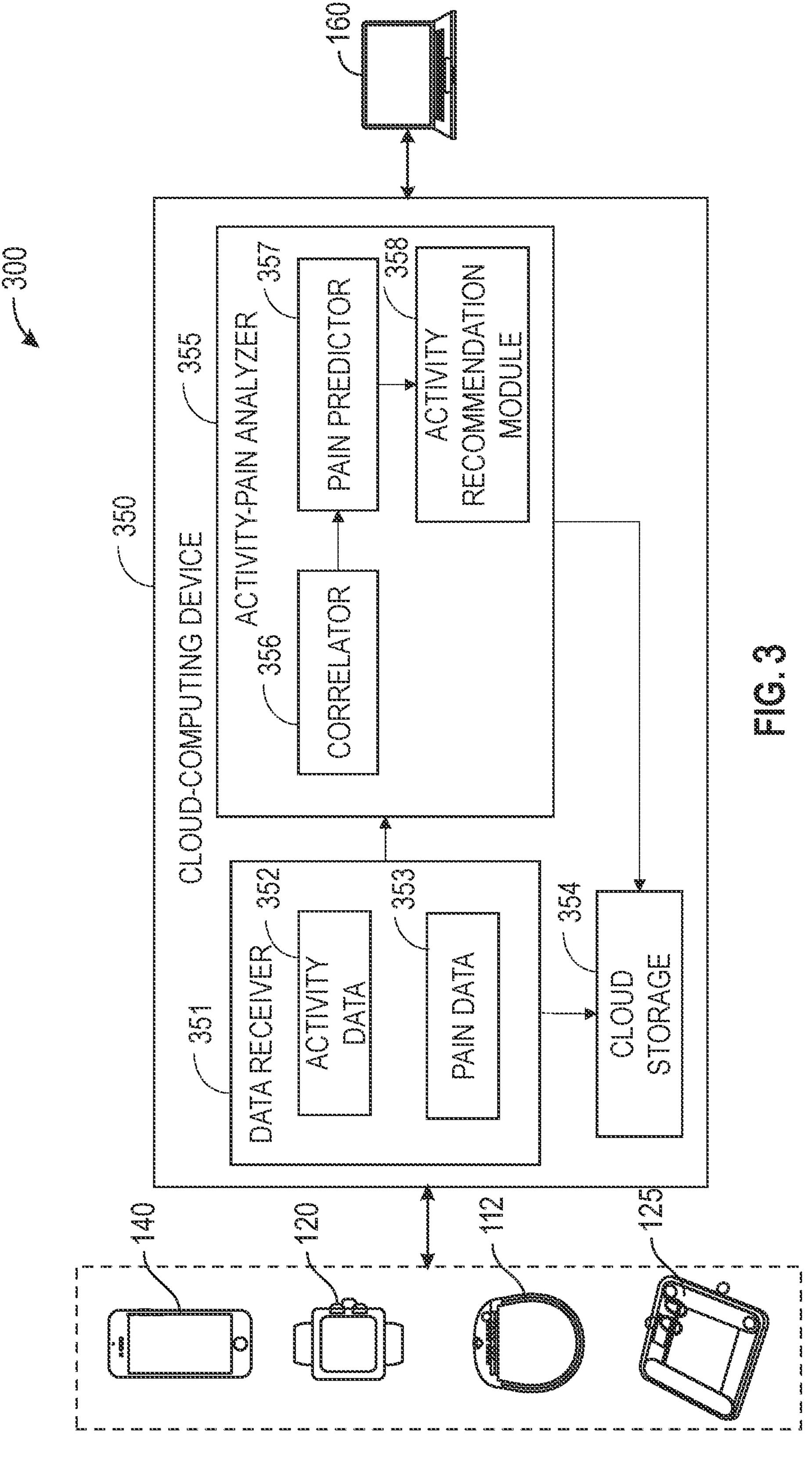
FIG. 3 illustrates generally an example of a cloud-based pain management system that predicts pain using physical activity information, which is an example of the cloud-based patient monitoring and pain management system as shown in FIG. 1.

FIG. 3 illustrates generally an example of a cloud-based pain management system 300, which is an example of the cloud-based patient monitoring and pain management system 100. The system 300 may be used for remote monitoring of patient physical activity, among other physiological and functional parameters, evaluating pain felt by the patient, recommending behavior changes to promote pain relief, and adjusting pain therapy or recommending therapy adjustment if necessary.

The system 300 may include a cloud-computing device 350, and one or more devices that are in direct or indirect communication with the cloud-computing device 350, such as the IPG 112, the wearable device 120, the stationary sensors 125, the mobile device 140, or the user terminal 160. The cloud-computing device 350, which is an example of the cloud-computing device 150, can include a data receiver 351, a cloud storage 354, and one or more cloud-based services including an activity-pain analyzer 355. The data receive 351 can receive and process patient data including activity data 352 and pain data 353. The activity data 352 can include physical activity intensity data sensed by one or more sensors (e.g., an accelerometer) in the IPG 112, the mobile device 140, or the wearable electronic device 120. In some examples, the activity data 352 can include patient subjective input about the physical activity that the patient has engaged in such as provided via the mobile app on the mobile device 140. The pain data 353 may include physiological or functional information collected by one or more sensors in the IPG 112, or by one or more sensors in the wearable electronic device 120. In some examples, the pain data 353 can include patient subjective report of pain felt such as via the mobile app on the mobile device 140. As discussed above in reference to FIG. 1, the patient reported pain may include patient responses to a questionnaire, or a pain drawing with identifications of pain locations and optionally annotations of pain qualities (e.g., intensity, severity, duration, type, or pattern of pain).

Cloud-based services such as the activity-pain analyzer 355 can be implemented as a part of a microprocessor in cloud server, which may be a dedicated processor such as a digital signal processor, application specific integrated circuit (ASIC), microprocessor, or other type of processor for processing information. Alternatively, the cloud-based services may be implemented as a set of instructions (e.g., software) of performing the functions, methods, or techniques described herein. In the example as illustrated in HG. 3, the activity-pain analyzer 355 can include a correlator 356, a pain predictor 357, and an activity recommendation module 358. The activity data 352 and the pain data 353 can be acquired concurrently. A correspondence can be established between the activity data and the pain data at a particular time.

In an example, the activity-pain analyzer 355 may compute a pain score using the pain data 353. The pain score can be computed using signal metrics generated from one or more physiological and/or functional signals such as sensed by the sensors in the IPG 112 and the wearable electronic device 120. The signal metrics may include statistical parameters, such as signal mean, median, or other central tendency measures or a histogram of the signal intensity, among others. The signal metrics may include morphological parameters such as maximum or minimum within a specific time period such as a cardiac cycle, positive or negative slope or higher order statistics, or signal power spectral density at a specific frequency range, among other morphological parameters. The signal metrics may additionally include timing information such as a time interval between a first characteristic point in one signal and a second characteristic point in another signal. The pain score can be represented as a numerical or categorical value that quantifies the patient's overall pain symptom. In an example, a composite signal metric may be generated using a combination of a plurality of the signal metrics respectively weighted by weight factors. The combination can be linear or nonlinear. To compute the pain score, the activity-pain analyzer 355 may compare the composite signal metric to one or more threshold values or range values, and assign a corresponding pain score (such as numerical values from 0 to 10) based on the comparison. Alternatively, the activity-pain analyzer 355 may compare the signal metrics to their respective threshold values or range values, assign corresponding signal metric-specific pain scores based on the comparison, and compute a composite pain score using a linear or nonlinear fusion of the signal metric-specific pain scores weighted by their respective weight factors. In an example, the threshold can be inversely proportional to signal metric's sensitivity to pain. A signal metric that is more sensitive to pain may have a corresponding lower threshold and a larger metric-specific pain score, thus plays a more dominant role in the composite pain score than another signal metric that is less sensitive to pain. Examples of the fusion algorithm may include weighted averages, voting, decision trees, or neural networks, among others.

Similar to the pain score computed from the pain data 353, the activity-pain analyzer 355 may compute an activity score using the activity data 352. For example, from the sensed motor activity signal, a plurality of activity signal metrics indicative of patient motor control or kinetics can be generated, such as physical activity metrics, posture metrics, range of motion metrics, gait metrics, among others. The activity signal metrics may be combined to produce a composite activity signal metric. To compute the activity score, the activity-pain analyzer 355 may compare the composite activity signal metric to one or more threshold values or range values, and assign a corresponding activity score based on the comparison. In some examples, the activity score may be computed using physiological information (e.g., hear rate or blood pressure).

Figure 4:
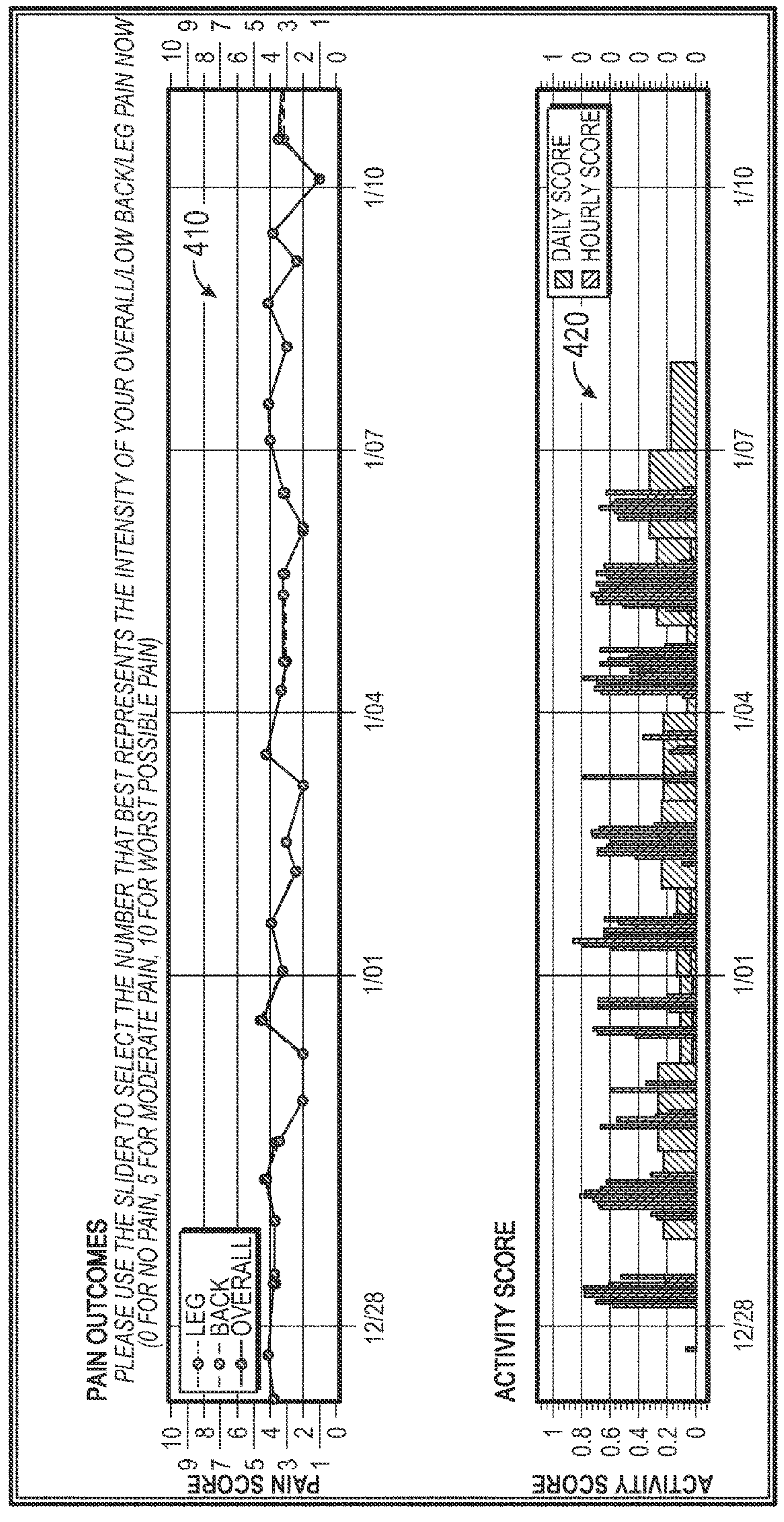
FIG. 4 illustrates generally example graphs of pain score trends and activity score trends.

The activity-pain analyzer 355 may trend the pain score and trend the activity score over time. FIG. 4 illustrates examples of a pain score trend 410 and an activity score trend 420. In some examples, pain scores can be computed respectively for pain felt at different body locations, such as leg and back. The respective pain scores can be trended over time to produce pain trends, such as a leg pain trend and a back pain trend, as illustrated in FIG. 4, in some examples, pain scores from different body locations may be aggregated to produce an overall pain score, which can be trended over time to produce an overall pain trend. In an example, the activity scores may be computed using activity data over specific time periods, such as every hour or every day, resulting in an hourly activity score trend or a daily activity score trend, as illustrated in FIG. 4.

The activity-pain analyzer 355 may establish a correspondence between one or more activity levels and one or more pain levels. This can be performed by the correlator 356, which can establish an activity-pain correlation using the activity data 352 and the concurrently collected pain data 353. In an example, the activity-pain correlation can be established using the pain score trend and activity score trend. The activity-pain correlation can indicate a degree of co-variation between the pain felt and the physical activity undertaken by the patient. From the correlation, the correlator 356 can determine a correspondence between one or more physical activities and one or more corresponding pain levels. In an example, the correspondence may be in a form of a lookup table. The correlator 356 may identify from the activity-pain correlation activities corresponding to different pain levels. For example, the correlator 356 may identify a first activity (also referred to as a "pain-causing" activity") that corresponds to worsened pain if the pain score is above a threshold or in a high score range. The correlator 356 may additionally or alternatively identify from the activity-pain correlation a second activity (also referred to as a "pain-free/pain-relieving activity") that corresponds to ameliorated pain if the pain score is below a threshold or in a low score range.

In some examples, pain-free/pain-relieving activities, and pain-causing activities, can be respectively determined using patient input such as provided via the mobile app on the mobile device 140. For example, during concurrent collection of the activity data 352 and the pain data 353, the patient can provide subjective descriptions of pain sensations including, for example, pain location, pain levels (e.g., numerical pain scales or categorical descriptors such as severe, mild, or no pain), types, patterns, among other pain quality descriptors. Such pain descriptors can be time-stamped such that they can be temporally associated with portions of the pain data and the activity data collected at the time of subjective pain description. In some examples, the activity-pain analyzer 355 can create one or more activity templates using such activity data, including, for example, a pain-causing activity template representing activities associated with worsened pain, a pain-free/pain-relieving activity template representing activities associated with no or ameliorated pain. The activity templates may be used to detect or predict a pain level from activity data acquired from the patient. Different activity templates may also be used to recognize or classify the detected activity as a pain-free/pain-relieving activity, or a pain-causing activity. In some examples, the activity templates may be used verify an activity the patient is undertaking. The patient may be notified, e.g., "Your recent activity is similar to a previous activity that you called pain-relieving activity." The patient may optionally confirm that the recent activity is indeed a pain-relieving activity.

The pain predictor 357 can predict pain levels for the physical activities detected from the patient using the activity-pain correlation. For example, physical activity data or the activity signal metrics generated therefrom may be compared to the previously identified activities corresponding to different pain levels (such as presented in a lookup table) to determine a pain level for the presently detected physical activity. In another example, the pain predictor 357 can compute an activity score using the physical activity data or the activity signal metrics, and determine the pain level based on the established correspondence between the activity score and the pain score. In yet another example, the pain predictor 357 can compute a similarity metric (e.g., a distance between features extracted from the data, or a correlation coefficient) between the physical activity data or the activity signal metrics generated therefrom and an activity template as discussed above, and determine a pain level for the presently detected physical activity based on the similarity metric.

The activity recommendation module 358 can generate activity recommendations based on the predicted pain. This may include, for example, recommendations to the patient to engage in, or increase engagement in, one or more identified pain-free/pain-relieving activities, and/or avoid or reduce engagement in those identified pain-causing activities. The recommendation may be provided to the patient via the communication link 180, such as being presented on a user interface of the mobile device 140, or presented on the wearable electronic device 120. Patient activities and the activity recommendations may also be provided to other authorized users such as a clinician via the user terminal 160.

In some examples, the cloud-computing device 350 can generate activity recommendations based on patient activity history. For example, the cloud-computing device 350 can determine from patient activity history an accumulated amount of activities a patient has engaged in over a specified observation period, such as a 24-hour period. The amount of activities can be represented by, for example, total time spent for performing certain activities that meet a criterion, such as exceeding an activity intensity threshold. In an example, the cloud-computing device 350 can include cloud-based services (e.g., software implementation of algorithms) that partition the activity data 352 (e.g., accelerometer data, heart rates, among other physiological or functional data indicative of activity) collected during an observation period into a plurality of intervals, such as one-minute intervals, analyze the activity data, and identify instances of the intervals with the activity data satisfying a specific condition (also referred to as "active intervals"). One example of such condition is the accelerometer data and heart rate data exceeding their respective threshold values. The amount of activity may be represented by the number of active intervals ($N_{active}$) during the observation period. If $N_{active}$ exceeds a threshold number $N_{TH}$, then an incentive, such as a notification may be provided to the patient on the mobile device 140 or the wearable electronic device 120 (e.g. "Good job!"). Conversely, if $N_{active}$ is below the threshold number $N_{TH}$, then a reminder, such as a notification on the mobile device 140 or the wearable electronic device 120 may be provided to the patient (e.g., "Increase your activities to at least two hours per day.").

In another example, the interval activity data (e.g., one-minute interval activity data) may be recognized as a pain-free/pain-relieving activity, or a pain-causing activity, such as based on a comparison to a pre-generated activity template, or based on a time-domain or frequency-domain analysis. The amount of activity can be calculated as the number of instances the interval activity being recognized as pain-free/pain-relieving activity (and such intervals are referred to as "pain-free activity intervals"), or the number of instances the interval activity being recognized as pain-causing activity (and such intervals are referred to as a "pain-causing activity intervals"). If the number of pain-free activity intervals ($N_{PF}$) corresponding to pain-free/pain-relieving activity X exceeds a threshold number $N_{TH1}$, then the patient may be incentivized to continue the activity, such as a notification provided to the patient on the mobile device 140 or the wearable electronic device 120 (e.g., "Good job! Continue doing activity X at current level."). Conversely, if $N_{PF}$ is less than the threshold number $N_{TH1}$, then the patient may be reminded to increase the pain-free/pain-relieving activities, such as a notification displayed on the mobile device 140 or the wearable electronic device 120 (e.g., "Activity X has a pain-relief effect. Increase your activity X to at least two hours per day."). If the number of pain-causing activity intervals ($N_{PC}$) corresponding to pain-causing activity Y exceeds a threshold number $N_{TH2}$, then the patient may be alerted to refrain from engaging in such activity Y, such as a notification displayed on the mobile device 140 or the wearable electronic device 120 (e.g., "Activity Y may cause or aggravate pain. Avoid activity Y in the future."). Information about patient engagement in pain-free/pain-relieving activities and pain-causing activities may also be accessed by other authorized users, such as via the user terminal 160.

In some examples, the cloud-computing device 350 can include cloud-based services that monitor patient progression towards a preset activity target (e.g., activity intensities and durations), or patient compliance with a preset activity schedule, both of which can be prescribed by a clinician. Feedback and recommendations may be provided to the patient or other authorized users based on patient performance with respect to the preset activity target. For example, incentives may be provided to the patient if the patient engages in sufficient amount of pain-free/pain-relieving activities and progresses towards the activity target. Conversely, if the patient fails to engage in adequate pain-free/pain-relieving activities and lag behind the activity target, a reminder may be provided to the patient.

The cloud storage 354 can store the activity data 352 and the pain data 353, among other data received by the data receiver 351. The cloud storage 354 can store processed data produced by one or more cloud-based services such as the activity-pain analyzer 355, including, for example, activity-pain correlations, correspondence (e.g., in a form of a lookup table) between the activity scores and pain scores, pain predictions and activity recommendations, among others. The stored data may be accessed by the wearable electronic device 120, the external system 130, the mobile device 140, or one or more user terminals 160. For example, a clinician may use an application installed on the user terminal 160 to securely access the cloud storage 354 and review the stored data, and make modifications to device parameters for the IPG 112 such as to adjust pain therapy.

Figure 5:
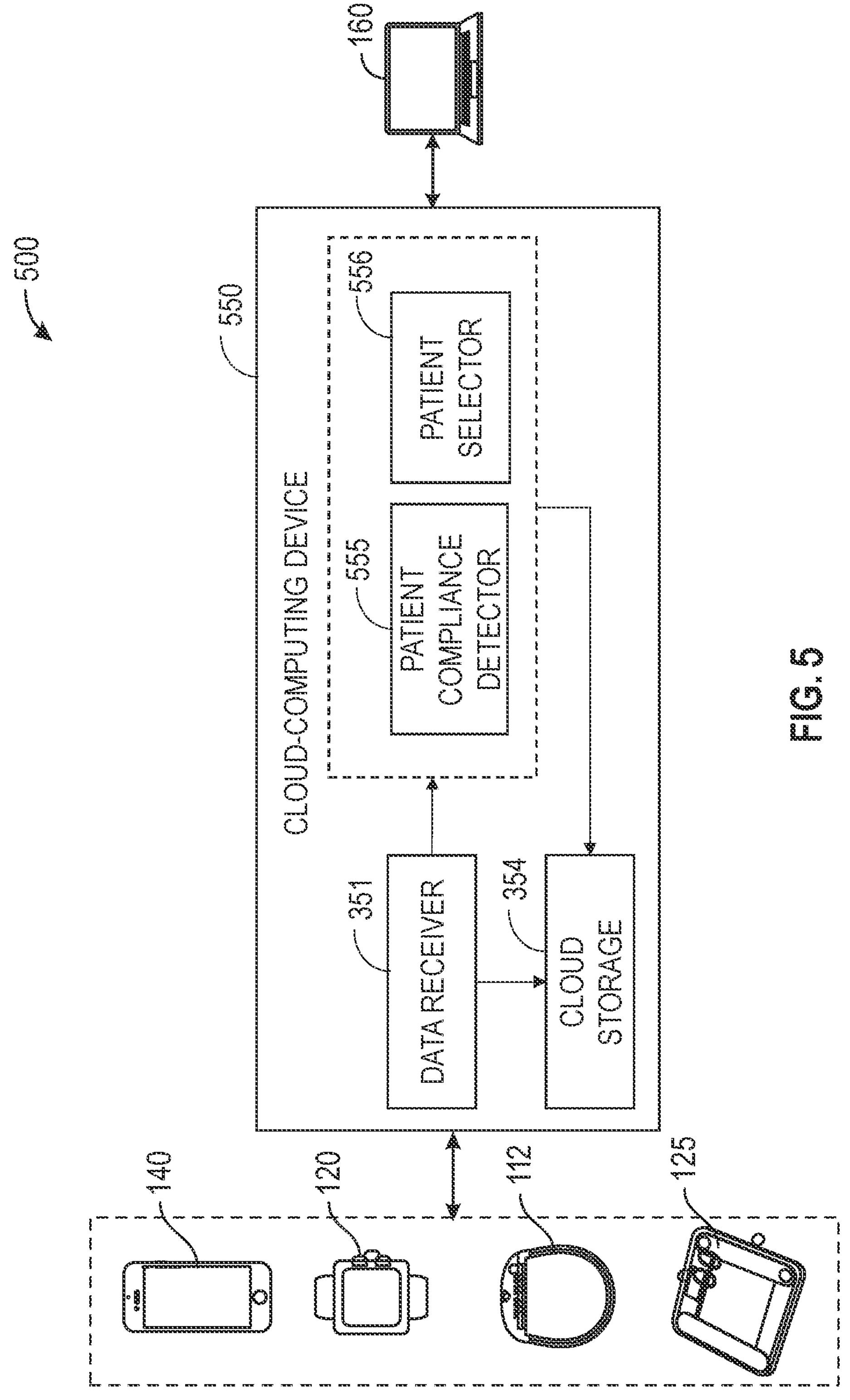
FIG. 5 illustrates generally an example of a cloud-based patient monitoring system, which is an example of the cloud-based patient monitoring and pain management system as shown in FIG. 1.

FIG. 5 illustrates generally an example of a cloud-based patient monitoring system 500, which is an example of the cloud-based patient monitoring and pain management system 100. The system 500 can remotely monitor patient behavior, determine if the patient complies with a clinical protocol (such as a data collection protocol), or to qualify the patient to enroll in a clinical study.

The system 500 can include a cloud-computing device 550 configured to communicate directly or indirectly with one or more networked devices including, for example, the IPG 112, the wearable device 120, the stationary sensors 125, the mobile device 140, and the user terminal 160. The cloud-computing device 550 can include a data receiver 351, a cloud storage 354, and one or more cloud-based services including a patient compliance detector 555 and a patient selector 556. The patient compliance detector 555 can detect patient compliance with a clinical protocol using the received data. In an example, the clinical protocol can include a data collection protocol that specifies a minimum amount of data to be collected from the patient, or a minimum amount of time for a specific sensor to actively collect data from the patient, within a specific time period such as a day, a week, or a month. In an example where data can be collected by sensors included in or associated with the wearable electronic device 120 only when it is worn on the patient, the data collection protocol can include a minimum amount of time to wear the wearable electronic device 120, such as at least 16 days in a rolling 30-day time window, or at least 10 hours per day. The patient compliance detector 555 can detect a data collection pattern using the received data, and determine an indicator of patient compliance with the data collection protocol using the detected data collection pattern.

The cloud-computing device 550 can generate trends of the received data, and detect quality data portions that satisfy a specific quality standard, such as a signal-to-noise ratio (SNR) exceeding a SNR threshold, or that the data are collected at a specific time or under a specific condition. In an example, the quality data portions include portions of the physiological signals that are collected when the patient is undertaking certain physical activities, or in a certain physician condition. The patient compliance detector 555 can calculate the time span of quality data portion ($T_Q$), such as number of days within a 30-day period or number of hours within a 24-hour period. In some examples, the time span of quality data portion ($T_Q$) may be determined using patient historical trends of wearing the wearable electronic device 120. In an example, the time span of quality data portion ($T_Q$) may be determined using patient historical trends of charging the wearable electronic device 120. In another example, the quality data portion includes quality PRO data provided by the patient, as discussed below with regard to the data quality controller 759 in FIG. 7. The time span of quality data portion ($T_Q$) may be determined using patient historical trends of providing quality PRO data.

The patient compliance detector 555 can determine that the patient is in compliance with the clinical protocol if $T_Q$ exceeds a threshold time ($T_{TH}$), or that the patient is non-compliant with the protocol if $T_Q$ is below the threshold $T_{TH}$. For example, the patient is deemed in compliance with the protocol if quality data are collected for at least 16 days in a rolling 30-day time window, or at least 10 hours in a 24-hour period. The cloud-computing device 550 may provide feedback to the patient and/or the clinician about compliance status. In an example, the threshold $T_{TH}$ represents a minimum device wearing time. In response to a detected compliance, an incentive may be provided to the patient (e.g., displaying on the mobile device 140 or the wearable electronic device 120 a notification "You wore the smart watch in 21 days in the past 30 days. Good job!"). In response to patient non-compliance, a reminder may be provided to the patient, to comply with the clinical protocol (e.g., displaying on the mobile device 140 or the wearable electronic device 120, "You wore the smart watch in 10 days in the past 30 days. Try to wear the smart watch for at least 16 days in the next 30 days."). In some examples, if the patient is predicted to be non-compliant such as based on historical wearing trends, the patient can be alerted before actual non-compliance is detected, such as by displaying "You are not on pace to hit 16-day watch-wearing threshold. Please wear the watch more frequently."

Patient compliant status may be used by the patient selector 556 to identify appropriate candidates to enroll in a clinical study, such as a trial for remote patient monitoring and data collection. In an example, the patient selector 456 can compute a patient compliance score based on appointment visits, physician contacts, usage of the IPG 112 etc. Patients with the compliance score exceeding a threshold can be qualified for enrollment in the clinical study, and patients with the compliance score below the threshold can be disqualified for enrollment in the clinical study. The compliance score and patient qualification status may be stored in the cloud storage 354, and/or provided to a user such as displayed on the mobile device 140, the wearable electronic device 120, or the user terminals 160.

Figure 6:
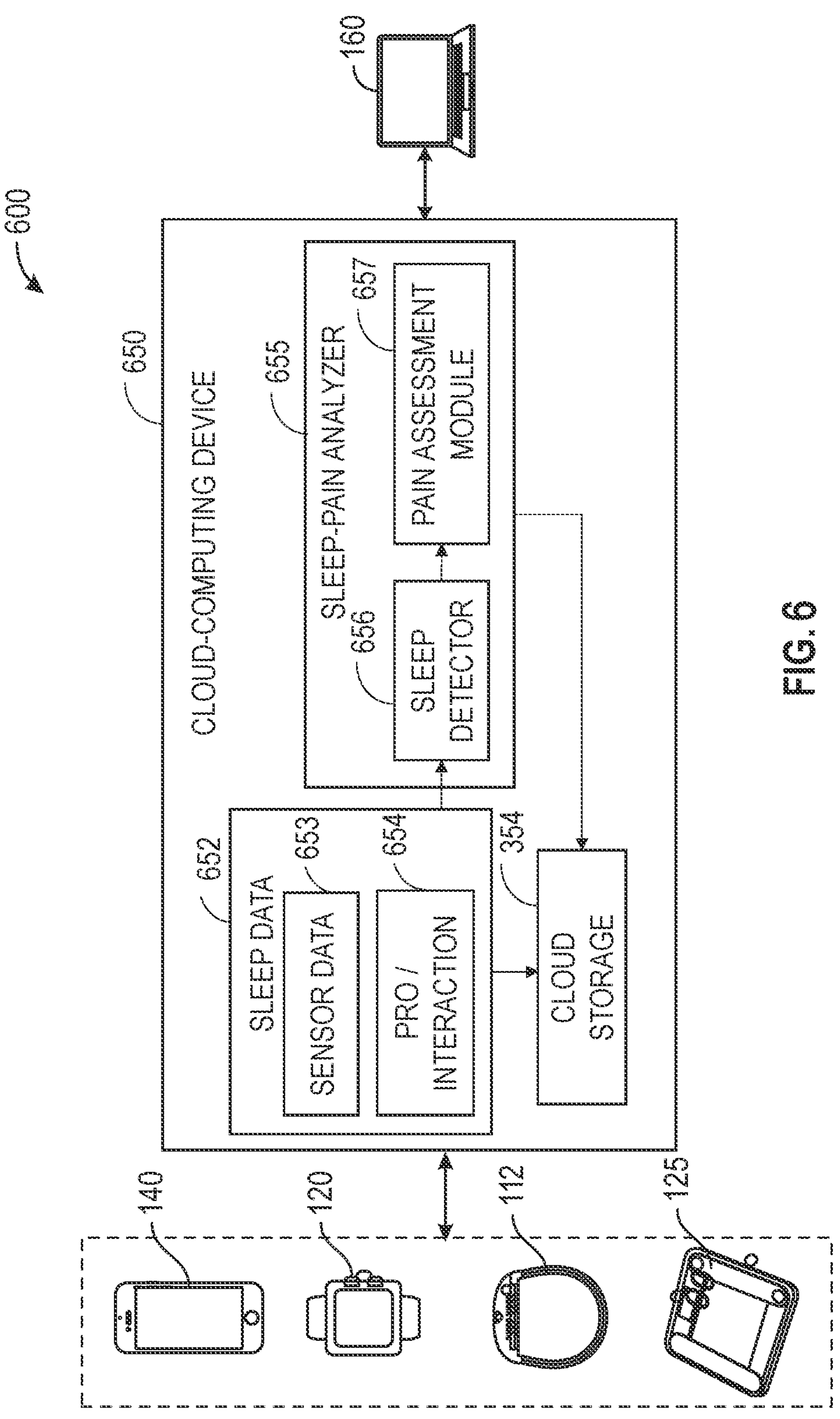
FIG. 6 illustrates generally an example of a cloud-based pain management system that predicts pain using information about sleep or awakening state, which is an example of the cloud-based patient monitoring and pain management system as shown in FIG. 1.

FIG. 6 illustrates generally an example of a cloud-based pain management system 600, which is an example of the cloud-based patient monitoring and pain management system 100. The system 600 may be used to remotely monitor, among other physiological and functional parameters, patient sleep state, evaluate pain felt by the patient, adjust pain therapy if necessary, and make recommendations of behavior change to promote pain relief. Patients in chronic pain may experience poor sleep quality such as shorter sleep duration, increased sleep disturbance, or frequent body position switches during sleep. Poor sleep quality such as increase sleep disturbance can be correlated to greater pain intensity, depression, and other physical and mental symptoms. Short sleep times, fragmented sleep, and poor sleep quality often causes heightened sensitivity to pain. Therefore, close monitoring of patient sleep disturbance may provide an objective assessment of pain, and may be used to improve pain therapy efficacy.

The system 600 may include a cloud-computing device 650, and one or more networked devices directly or indirectly in communication with the cloud-computing device 350 including the IPG 112, the wearable device 120, the stationary sensors 125, the mobile device 140, and the user terminal 160. The cloud-computing device 650 can include a data receiver 351, a cloud storage 354, and one or more cloud-based services including a sleep-pain analyzer 655. The data receiver 351 can receive and process patient data including sleep data 652. The sleep data 652 can include sensor data 653 indicative of patient sleep or awakening state, which can be sensed from the patient by one or more sensors included in the IPG 112, the wearable device 120, or the mobile device 140. The sensor data 653 may include physiological or functional data as discussed above with reference to FIG. 1. By way of example, sensor for collecting the sensor data 653 may include one or more of: an accelerometer to sense an accelerometer signal indicative patient physical activity or functional state; a gyroscope such as a three-axis gyroscope to sense a gyroscope signal indicative of posture; an electrocardiogram (ECG) sensor to sense an ECG signal; a heart rate signal; a heart rate variability (HRV) signal; a blood oxygen saturation (SpO2) level signal; an electroencephalogram (EEG) sensor to sense an EEG signal; a temperature sensor to sense body temperature such as skin temperature; peripheral body temperature, or core body temperature, an electrodermal activity (EDA) sensor to measure a skin conductance signal, such as from patient's hand, wrist, or foot; a blood volume pulse (BVP) sensor to sense a BVP signal, such as a photoplethysmography (PPG) sensor operably positioned adjacent to an artery to detect pulsatile information from the artery to compute the BVP signal; and an impedance sensor to measure a bioelectric impedance signal such as skin impedance.

The sleep-pain analyzer 655 can include a sleep detector 656, and a pain assessment module 657. The sleep detector 656 can process sleep data 652, generate therefrom one or more sleep parameters, and detect a sleep or awakening state of the patient using the sleep parameters. The sleep parameters may include, for example, sleep incline, sleep sidedness, frequency of sleep position switch, or other sleep quality or sleep disturbance metrics. For example, an increase in sleep incline, or enhanced frequency of body position switches during sleep, or reduced sleep duration are indicators of increase pain.

In some examples, the one or more sleep parameters have values indicative of the patient's sleep stages. For example, the values of the one or more sleep parameters can be mapped to the sleep stages using data collected from the patient or collected from a patient population. Sleep stage can be classified as, but not being limited to, awake, slow-wave sleep, REM sleep, non-REM1 sleep, or non-REM2. The sleep detector 656 can detect whether the patient is asleep or awake, and further the particular sleep stage if the patient is detected asleep. Analysis of the one or more sleep parameters can result in the current sleep stage of the patient as well as time and/or percentage of time spent in each sleep stage.

In some examples, the sleep detector 656 can compute a sleep score using an outcome of the analysis of the one or more sleep parameters. The sleep score can indicate a probability of being asleep (or a probability of being awake). The sleep score can indicate a probability of being in a particular sleep stage. In some examples, the sleep score may represent a sleep quality based on, for example, hours of sleep, sleep disturbance or interruptions, etc. The sleep score can include a number (numerical value), a sleep signal metric, and/or a number being a function of the sleep signal metric. For example, value ranges each corresponding to one of sleep stages may be determined for each of the one or more sleep parameters for the patient, and used for computing the sleep score as a function of the sleep stage.

In some examples, the sleep detector 656 can generate a sleep signal metric using the one or more sleep parameters, such as a linear or nonlinear combination of multiple sleep parameters. The combination of multiple sleep parameters may include weighted combination of sleep parameters each scaled by respective weighting factors. The sleep detector 656 can compute the sleep score using the sleep signal metric. In an example, the sleep detector 656 can trend the sleep signal metric over time, and compute the sleep score using the resulting trending of the sleep signal metric. For example, the sleep detector 656 can detect the sleep state in response to one or more of a detected physical activity level falling below a threshold activity level; a detected $SpO_2$ level falling below a threshold $SpO_2$ level; a detected heart rate (HR) falling below a HR threshold; a detected heart rate variability (HRV) exceeding a HRV threshold; a peripheral temperature or a core temperature falling below a temperature threshold, etc. In some examples, the sleep detector 656 may compute a sleep score indicative of probability of being asleep using a combination of the detected parameters (e.g., the detected physical activity level, $SpO_2$ level, HR, or HRV)) relative to (e.g., deviations from) their respective thresholds. The sleep detector 656 can determine that the patient is asleep if the sleep score exceeds a first threshold, or awake if the sleep score is below a second threshold lower than the first threshold. If the sleep score falls between the first and second threshold, additional testing may be performed or a patient confirmation may be requested to determine the sleep or awakening state.

In addition or alternative to the sensor data 653 such as physiological and functional signals, the sleep data 652 may include PRO/interaction 654 data representing patient interaction with the mobile device 140 or the wearable electronic device 120. The PRO, as discussed above with reference to FIG. 1, and patient interaction with devices such as the mobile device 140 or the wearable electronic device 120, may be indicative of sleep or awakening state. For example, the mobile device 140 may track patient operation of the device, such as activation of mobile apps or switching between different mobile apps on the mobile device 140. The sleep detector 656 can determine that the patient is awake if it is detected that the patient interacts with the mobile device 140.

In some examples, the mobile app on the mobile device 140 may push a notification on the user interface, such as a message "Are you awake", prompting the user for a confirmation within a response detection period. The patient is deemed awake if the patient provides a confirmation, or is deemed asleep if the notification is ignored (i.e., no response provided within the detection period, during which no other app activation or switching is detected). In another example, the mobile app on the mobile device 140 may push a reminder, such as "Please charge your smart watch now", or "Please dim the light of your mobile phone", or other sleep hygiene remainders. The patient is deemed awake if the reminded action gets activated, or is deemed asleep if the reminder gets ignored. In another example, the mobile app on the mobile device 140 may produce an alert, and track patient reaction to the alert within a response detection period. The alert can be in a form of textual or graphical alert. The alert can be gentle vibration (to avoid disrupting sleep). The patient is deemed asleep if the alert is ignored, or is deemed awake if the alert is stopped or interrupted within the detection period. In yet another example, the mobile app may receive from the mobile device 140 accelerometer data indicative of patient motion. The sleep detector 656 may detect the sleep or awakening state based on the accelerometer data. For example, if the accelerometer data exceed a threshold may indicate patient holding, moving, and manipulating the mobile device, in which case the patient is deemed awake.

In some examples, the mobile app on the mobile device 140 may push notifications, alerts, or reminders only at times when the patient is expected to sleep. The expected bedtime can be set manually by the patient. Alternatively, the expected bedtime can be automatically determined based on patient historical bedtimes.

The pain assessment module 657 can assess patient pain based on the analysis of the sleep data. In an example, the pain assessment module 657 can trend a sleep parameter over time, assess sleep quality of the patient, and predict pain based on the trend of the sleep parameter. A sustained poor sleep quality such as increased sleep disturbance can indicate worsening of pain, or non-optimal or lack of effectiveness of present pain therapy. The pain assessment module 657 may provide recommendations to adjust one or more pain therapy parameters, such as stimulation parameters used by the IPG 112 to generate and deliver a neuromodulation therapy such as SCS. In various embodiments, the pain assessment module 657 can optimize the stimulation parameters for the determined sleep state. In various embodiments, the pain assessment module 657 can execute a closed-loop neurostimulation algorithm to determine optimal stimulation parameters using the sleep state as an input.

The cloud storage 354 can store the activity data 352 and the pain data 353, among other data received by the data receiver 351. The cloud storage 354 can store processed data produced by one or more cloud-based services such as the sleep-pain analyzer 655. The stored data may be accessed by the wearable electronic device 120, the external system 130, the mobile device 140, or one or more user terminals 160. For example, a clinician may use an application installed on the user terminal 160 to securely access the cloud storage 354 and review the stored data, and make modifications to device parameters for the IPG 112 and adjust pain therapy.

Figure 7:
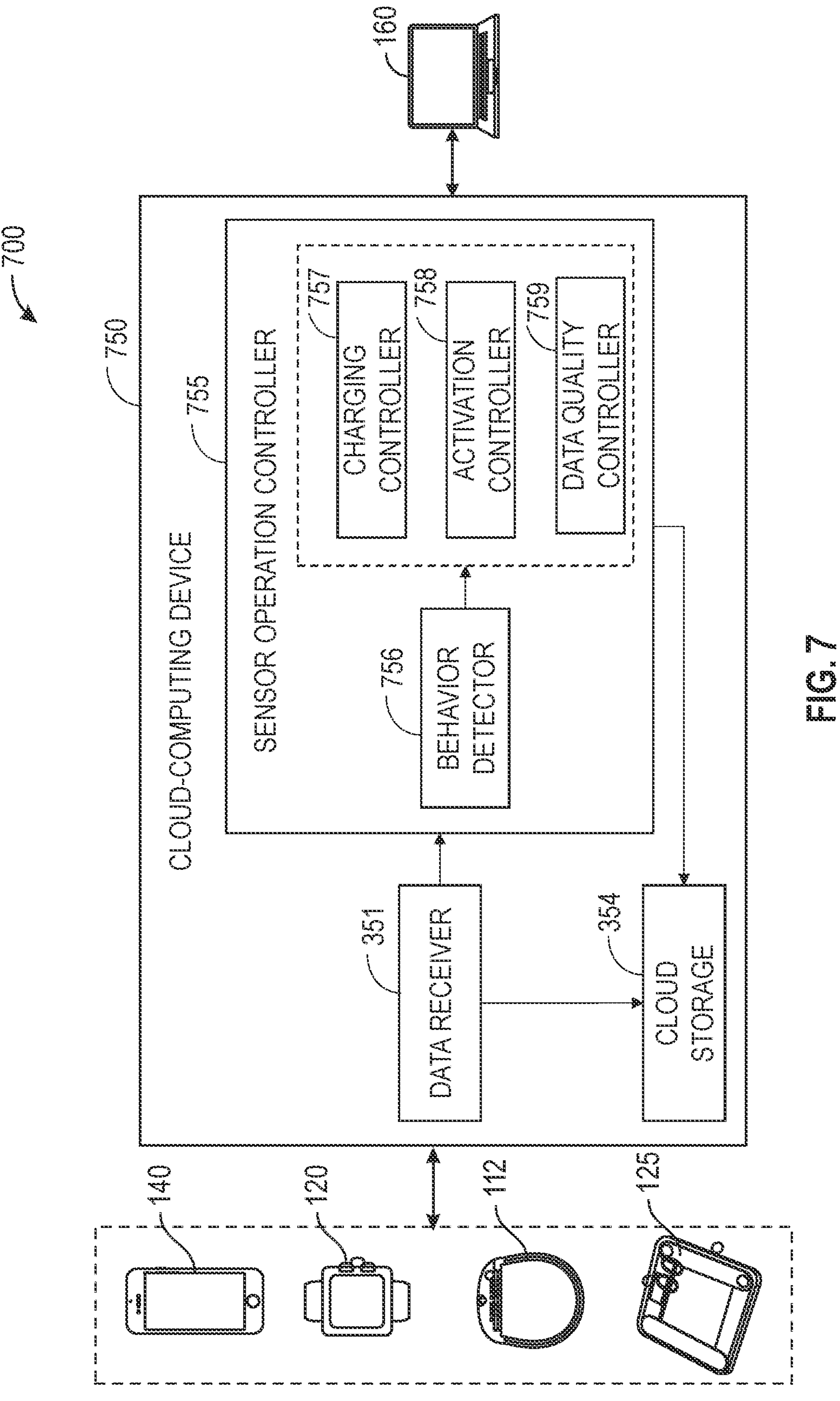
FIG. 7 illustrates generally an example of a cloud-based patient monitoring and device control system, which is an example of the cloud-based patient monitoring and pain management system as shown in FIG. 1.

FIG. 7 illustrates generally an example of a cloud-based patient monitoring and device control system 700, which is an example of the cloud-based patient monitoring and pain management system 100. The system 700 can remotely monitor patient behavior, and adjust operations of one or more of the wearable electronic device 120, the mobile device 140, the stationary sensors 125, or the IPG 112, or operations of one or more sensors in any of such devices, based on the patient behavior. In an examples, the system 700 can generate and provide to the patient or other authorized users (e.g., a clinician) sensor or device operation recommendations.

The system 700 may include a cloud-computing device 750, and one or more networked devices directly or indirectly in communication with the cloud-computing device 350 including the IPG 112, the wearable device 120, the stationary sensors 125, the mobile device 140, and the user terminal 160. The cloud-computing device 750 can include a data receiver 351, a cloud storage 354, and one or more cloud-based services including a sensor operation controller 755. The sensor operation controller 755 can include a behavior detector 756 configured to detect patient functional state, such as a physical activity or a sleep state, from the received patient data. The sensor operation controller 755 can include one or more of a charging controller 757, an activation controller 758, or a data quality controller 759, each controlling respective aspects of sensor or device operations in accordance with the detected patient behavior, and/or providing recommendations to the patient or authorized users.

The charging controller 757 can generate a control signal or a reminder to the patient to charge a rechargeable battery that powers one or more sensors in a device (e.g., the wearable electronic device 120, the mobile device 140, the stationary sensors 125, or the IPG 112). In an example, the wearable electronic device 120 includes one or more battery-powered sensors configured to collect physiological or functional data from the patient only when such device is worn on the patient. To charge the wearable electronic device 120, the device is typically removed from the patient, and the data collection is discontinued. To prevent disruptions to data collection or physiological tracking due to device charging, the charging controller 757 can generate a reminder to the patient to charge the wearable electronic device 120 at times when it is least likely to collect important data or to perform physiological tracking. The charging controller 757 may additionally or alternatively send a reminder to the patient at time prior to incidents where it is most desirable to avoid dead battery. For example, if it is desirable to collect data when the patient is in a particular physiological or functional state (e.g., during sleep) or being engaged in a particular physical activity, then the charging controller 757 can provide a reminder to the patient to charge the wearable electronic device 120 at a specific time (e.g., at least one hour) prior to the anticipated physiological or functional state or the activity. In an example, the charging controller 757 can identify trends of physiological or functional state or activity from the received patient data, predict timing for the next physiological or functional state or activity of interest based on the trends, and generate a reminder to the patient to charge the wearable electronic device 120 prior to the predicted physiological or functional state or the activity. In another example, the patient data received by the data receiver 351 may include user input of schedules for certain activities as a part of the PRO, such as a physical activity schedule or a sleep schedule, and the charging controller 757 can generate a reminder to the patient to charge the wearable electronic device 120 in accordance with the activity schedule provided by the patient. In some examples, the charging controller 757 can generate the reminder to charge the wearable electronic device 120 based on historical device battery usage pattern and/or charging history. The reminders can include graphical, textual, or vibrational notifications displayed or otherwise presented on the mobile device 140 or the wearable electronic device 120.

Figure 8:
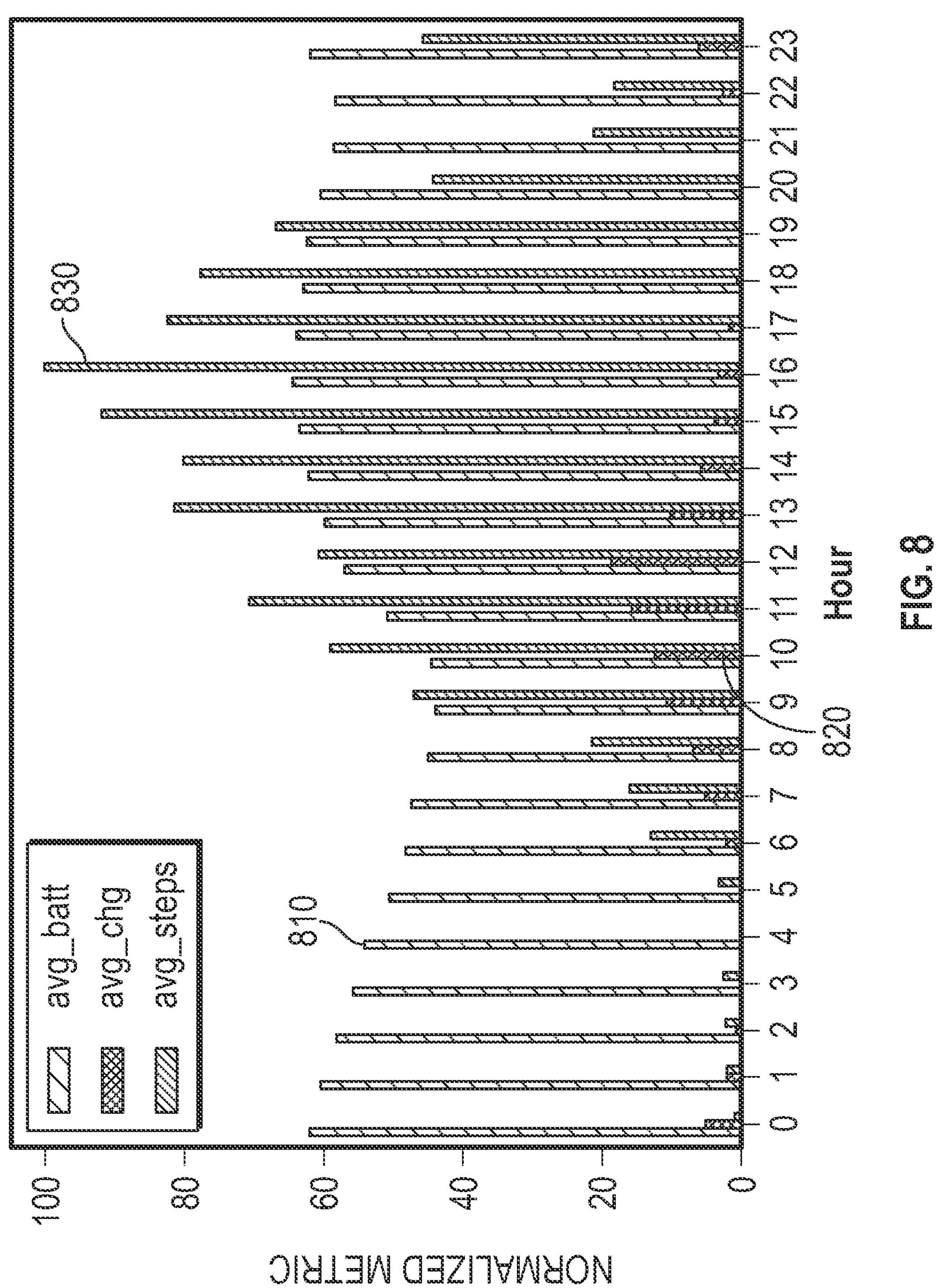
FIG. 8 illustrates generally example graphs of a battery status trend and a battery charging pattern of a smart wearable device worn by a patient, along with a patient physical activity trend.

By way of example and not limitation, FIG. 8 illustrates examples of a battery status trend 810 and a battery charging pattern 820 of a smart wearable device worn by a patient, along with a patient physical activity trend 830. The battery status trend, battery charging pattern, and the patient physical activity trend include respective hourly measurements over a 24-hour period. The hourly measurements are generated by averaging respective historical data collected by the smart wearable device during that hour. The battery status trend 810 represents a trend of remaining battery level out of 100% (a fully-charged battery level). The battery charging pattern 820 represents the patient's charging behavior within each hour. For example, 100% indicates the watch was charged for the entire hour, 80% indicates that the watch was charged 80% of an hour (i.e., about 48 minutes), and 0% indicates that the watch was never charges during that hour. The physical activity trend 830 is represented by the number of steps the patient took, such as counted by a pedometer in the smart wearable device, during each hour, normalized by the maximum hourly step count within the 24-hour period (which occurs between 16:00-17:00 in this example). As illustrated in FIG. 8, the battery status trend 810 shows a decreasing trend over the night and extending to the morning at around 7:00-8:00 a.m. The physical activity trend 830 shows that the patient wakes up and picks up physical activity during the daytime, which peaks at around 15:00-16:00. The battery charging pattern 820 coincides with at least an earlier phase of the physical activity trend 830, where charging begins when the patient wakes up, and reaches the peak at 11:00-12:00 p.m. To ensure undisruptive data collect using the smart wearable device during the time of active physical activities, the charging controller 757 can generate a reminder to the patient to charge his wearable device at least several hours prior to the morning physical activities, such as during the night. If it is desirable to collect data during sleep (such as required by a protocol of a clinical study of which the patient is a participant or a candidate), the charging controller 757 can generate a reminder to the patient to charge his wearable device at least several hours prior to bedtime, and to wear the device throughout the night.

In some examples, sensor or device operations may be adjusted based on a battery level of the rechargeable battery that powers the one or more sensors in a device (e.g., the wearable electronic device 120, the mobile device 140, the stationary sensors 125, or the IPG 112). Notification of the battery level, and device or sensor operation recommendations or reminders, may be provided to the patient or other authorized user. For example, when the battery level is below a threshold level (e.g., 15%), the device (e.g., the wearable electronic device 120) may reduce data sampling rate, reduce data collection period, or change data collection schedules for one or more sensors, or deactivate (turn off) certain sensors. Additionally or alternatively, a low-battery alert may be provided to the patient, optionally along with a recommendation to immediately charge the battery, or adjust sensor data collection schedules, among other changes to sensor or device operations.

Returning to FIG. 7, the activation controller 758 can generate a control signal to adjust operations of one or more sensors based on the detected patient behavior. Operating the sensors to adapt to patient behavior can help save battery power while maintaining high-quality data collection at desirable times or occasions. In an example, adjusting the sensor operation can include selectively activating (switching on) or deactivating (switching off) a sensor to collect data from the patient. In another example, adjusting the sensor operation can include adjusting a data acquisition schedule for a sensor. The data acquisition schedule can be a time-based schedule, such that the sensor is turned on or off at respective pre-determined time and duration. Alternatively, the data acquisition schedule can be an event-trigged schedule, such that the sensor is turned on or off based on a detection, or a prediction of occurrence, or a specific event such as sleep or a particular physical activity. In some examples, adjusting the sensor operation can include adjusting a sampling rate or data collection duration for one or more sensors. For example, the activation controller 758 can send a control signal to reduce the sampling rate of sensor circuits when the behavior detector 756 detects that the patient is asleep, and increase the sampling rate when the patient is detected to be awake. In an example, the sampling rate or the duration of data collection can be proportional to the physical activity level. In another example, the activation controller 758 can send a control signal to switch off certain highly sensitive sensors (e.g., PPG or blood oxygen level sensors) when the behavior detector 756 detects a physical activity level exceeding a threshold indicating the patient is engaging in strenuous physical activities. The highly sensitive sensors can be switched back on when the detected physical activity level falls below the threshold.

The data quality controller 759 can detect sensor anomaly using the data collected by a sensor, and generate an indication of the detected sensor anomaly to a user (e.g., the patient via the mobile device 140 or the wearable electronic device 120), or a clinician via the user terminal 160). The sensor anomaly may be represented by poor data quality indicative of, for example, poor contact with the patient. In an example of detecting anomaly of sensors included in or associated with a wearable device such as the wearable electronic device 120, the sensor anomaly may be indicative of the wearable device being incorrectly worn, too loosely or too tightly worn, or otherwise misplaced on the patient. The data quality controller 759 may compute a sensor data quality score from a physiological signal sensed by the sensor. The sensor data quality score can be computed using a template matching between the sensed physiological signal (or signal feature extracted therefrom) and a pre-generate template representing the signal (or extracted signal features) sensed by the same type of sensor under a known, anomaly-free condition where the wearable device is appropriately worn and the data captured during a controlled condition such as a device training session. Alternatively, the sensor data quality score can be computed based on frequency-domain analysis of the sensed physiological signal. If the sensor data quality score exceeds a threshold, the wearable device is deemed properly worn and the sensors properly collect the data. If the sensor data quality score falls below the threshold, the data quality controller 759 can generate an alert such a notification to the user to check if the wearable device is properly worn. Additional information on how to properly wear the device can be provided to the patient, such as displayed on the user interface of the wearable electronic device 120 or the mobile device 140. In an example, the data quality controller 759 can present to the patient a recommendation to correct misplacement of the wearable device.

In some examples, the data quality controller 759 can detect or confirm sensor anomaly using cross-validation between measurements obtained from two or more sensors. The two or more sensors can measure respective physiological parameters each indicative of whether or not the wearable device is properly worn on the patient. The physiological parameters corresponding to the respective sensors can be the same type of parameter (e.g., heart rate variability), or alternatively different types of parameters (e.g., one being heart rate variability, another being physical activity). The two or more sensors may reside in the same device, or alternatively in different devices (e.g., one sensor associated with the IPG 112, another sensor associated with the wearable electronic device 120 or the mobile device 140). By way of example and not limitation, a heart rate sensor associated with the IPG 112 can sense a heart rate, and a PPG sensor included in wearable electronic device 120 can sense a heart rate. The data quality controller 759 can use the PPG sensor-based heart rate to cross-validate the heart rate detected by the IPG 112. If the heart rates detected by both sensors are outside a normal range thus indicating improper wearing of the wearable electronic device, then the anomaly is confirmed, in which case the data quality controller 759 can generate an alert to the user. If the heart rate detected by the PPG sensor is inconsistent with the heart rate detected by the IPG-based heart rate (e.g., one sensor indicates proper wearing of the device but the other sensor indicates improper wearing of the device), then the sensor anomaly is not confirmed; in some examples, further validation such as a third heart rate sensor may be used to validate proper device wearing on the patient.

The cross-validation can additionally or alternatively be performed between sensor data and PRO data. In an example, when a sensor in the IPG 112, the wearable electronic device 120, or the mobile device 140 shows poor data quality indicative of improper device wearing on the patient, a notification may be displayed on the wearable electronic device 120 or the mobile device 140, and the patient is prompted to check if the device is worn, or to adjust the wearing of the device on the body. If the patient indicates that device is not worn, then a reminder to wear the device and be pushed to the user interface of the wearable electronic device 120 or the mobile device 140. If the patient confirms wearing of the device, a recommendation to adjust the device in accordance with training information on how to properly wear the device can be provided to the patient.

In some examples, the data quality controller 759 can detect qualities of PRO data. For example, some repeated user behaviors with respect to providing PROs may indicate that the patient has failed to provide consistently quality answers to the questions but rather just hit the same button to get through the questionnaire. In an example, the behavior detector 756 may analyze the PROs received by the data receiver 351, and identify patterns of patient answers such as: consistently providing the same answer for a question (e.g., regarding pain locations, levels, types, or patterns) over PROs provided over an extended period of time (e.g., multiple days or weeks); consistently picking "default" answer or leaving it blank; consistently selecting the top choice (e.g., the first choice) among the four candidate choices; etc. The data quality controller 759 can compute a PRO data quality score based on the analysis of the patient answers. If the PRO data quality score exceeds a threshold, the PRO protocol can be maintained. If the PRO data quality score falls below the threshold, the PRO protocol can be modified. Examples of the modification of the PRO protocol may include modifying answer locations, randomizing the order of choices or screen placement of buttons to avoid or reduce the chance of tapping in the same spot or selecting the same answer without careful reading and thinking; requesting confirmation of multiple choice with free text statement; or getting validity by asking similar questions multiple times such as over multiple days, etc.

Figure 9:
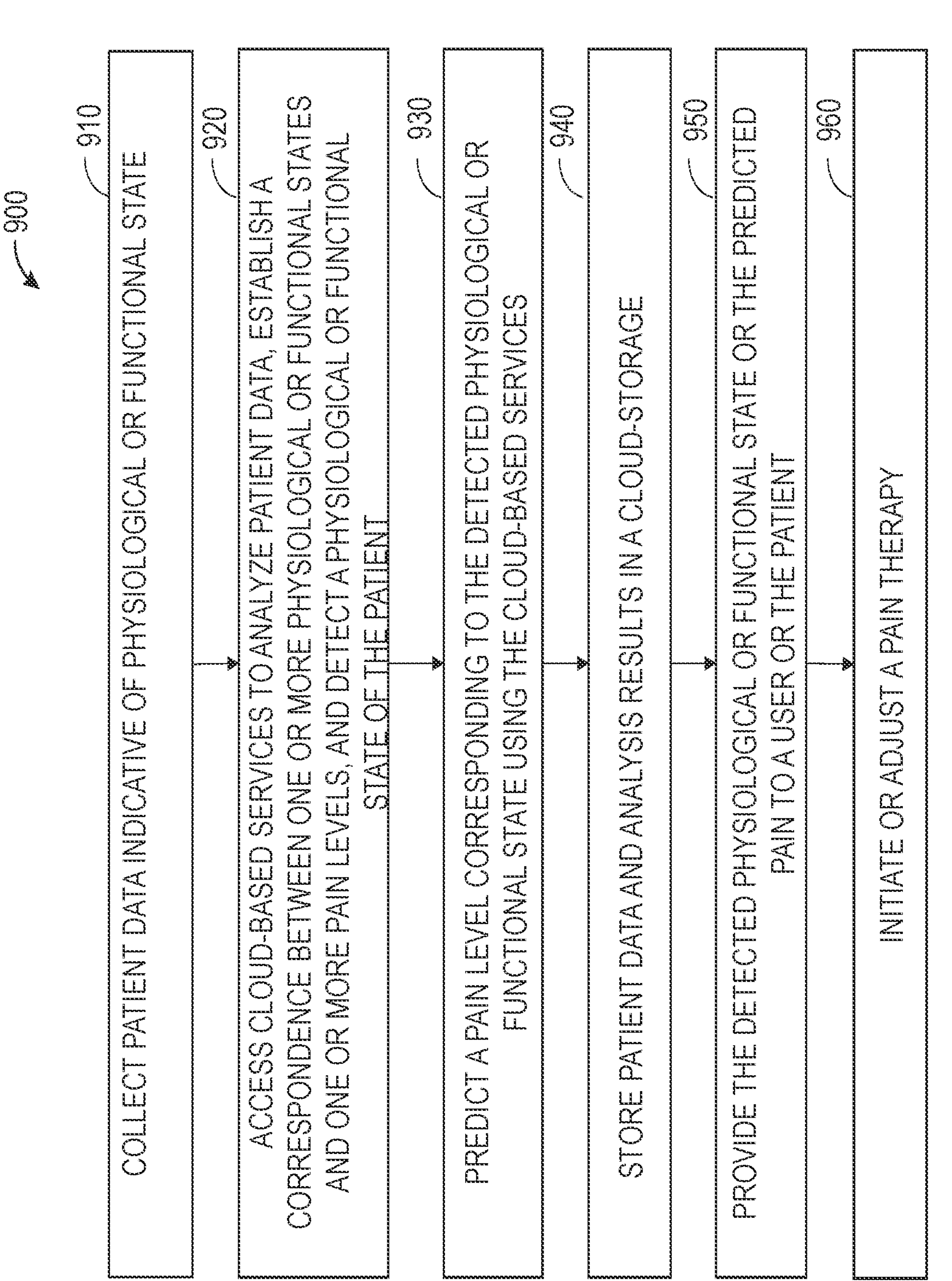
FIG. 9 illustrates generally an example of a method for remote monitoring and managing of a patient with an implantable device for pain management.

FIG. 9 illustrates, by way of example and not limitation, a method 900 for remote monitoring and managing of a patient with an implantable device, such as an implantable pulse generator (IPG), for pain management via a cloud-based system, such as the cloud-based patient monitoring and pain management system 100.

The method 900 begins at 910 where patient data indicative of physiological or functional state of the patient may be collected using one or more implantable or external devices, such as the IPG 112, the wearable electronic device 120, or the mobile device 140. The received patient data may include physiological information including cardiac electrical activity, electrocardiograms (ECGs), heart rate, heart rate variability, a photoplethysmography (PPG) signal, blood oxygen saturation (SpO2) such as derived from the PPG signal, blood pressure, a respiration signal, respiratory rate, tidal volume, galvanic skin response, maximum rate of oxygen consumption ($VO2_{max}$) during exercise, peripheral body temperatures, among others. The physiological information may be collected by physiological sensors included in or associated with the IPG 112, the wearable electronic device 120, or the mobile device 140. Examples of the functional signals may include a motor activity signal patient posture, gait, balance, or physical activity signals, a sleep state signal that contains information about sleep disturbance, among others. The functional signals may be collected by one or more sensors including, for example, an accelerometer, a gyroscope, a magnetometer (e.g., a compass), an inclinometer, a goniometers, an electromagnetic tracking system (ETS), or a global positioning system (GPS) sensor, among others. The patient data received at 910 may additionally or alternatively include patient reported outcome (PRO), which may include, for example, patient report on pain or paresthesia sensation (e.g., intensity, severity, duration, body location, or pattern of pain or paresthesia), effectiveness of pain therapy, patient report of activities, among others. The PRO can be received via a mobile app on the mobile device 140.

At 920, cloud-based services (e.g., software implementations of algorithms for data analysis) stored in the cloud-computing device 150 (or any of its variants such as cloud-computing devices 350, 550, or 650) may be accessed by the patient or an authorized user via a remote device, such as the wearable electronic device 120, the mobile device 140, or the user terminal 160. Using the cloud-based services, a correspondence between one or more physiological or functional states (e.g., physical activities levels, or sleep and awakening states) and one or more corresponding pain levels may be established. By analyzing the patient data, a physiological or functional state of the patient may be detected, such as patient engagement in physical activities, or a sleep or awakening state. In some examples, the cloud-based services may be used to determine if the patient complies with a clinical protocol (e.g., a protocol for data collection), or to qualify patients to enroll in a clinical study, as discussed above with reference to FIG. 5.

At 930, a pain level corresponding to the detected physiological or functional state may be predicted for the patient using the cloud-based services, including, for example, the established correspondence between one or more physiological or functional states and one or more pain levels. In an example, the patient data collected at 910 include activity data and pain data, and correspondence can be represented by an activity-pain correlation between the activity data and pain data, as described above with reference to FIG. 3. The activity data can include physical activity intensity data sensed by one or more sensors, such as an accelerometer, in the IPG 112 and/or the wearable electronic device 120, and patient input of the physical activity that the patient has undertaken, such as provided via a mobile app on the mobile device 140. The pain data may include physiological or functional information collected by one or more sensors in the IPG 112 and/or in the wearable electronic device 120, and patient input of pain felt such as via the mobile app on the mobile device 140. The activity-pain correlation represents a degree of co-variation between the pain felt and the physical activity undertaken by the patient. The activity-pain correlation may be represented by a lookup table or an association map between one or more physical activities and corresponding one or more pain levels. Activities corresponding to different pain levels may be identified from the activity-pain correlation, including, for example, pain-free/pain-relieving activities corresponding to ameliorated pain, and pain-causing activities corresponding to worsened pain. In some examples, PRO data provided by the patient may be used to help identify the pain-free/pain-relieving activities and/or the pain-causing activities.

A pain level may be predicted for the detected physiological or functional state using the activity-pain correlation and detected patient activity level, such by using the pain predictor 357. For example, physical activity data, or the activity signal metrics generated therefrom, may be compared to the previously identified activities that correspond to different pain levels (such as presented in a lookup table) to determine a pain level for the presently detected physical activity. In another example, an activity score may be computed using the physical activity data or the activity signal metrics, and determine the pain level based on the established correspondence between the activity score and the pain score. In yet another example, the pain level for the presently detected physical activity may be predicted using a similarity metric between the physical activity data or the activity signal metrics generated therefrom and an activity template.

Another example of predicting a pain level corresponding to the detected physiological or functional state at 930 involves an evaluation of patient sleep or awakening state, such as using the sleep detector 656 as described above with reference to FIG. 6. In an example, the sleep or awakening state can be detected using physiological or functional information collected from the patient, such as heart rate, heart rate variability, $SpO_2$, activity, or a combination of various physiological or functional information. In some examples, a sleep score indicative of probability of being asleep can be computed using the physiological or functional information. The patient is detected to be asleep if the sleep score exceeds a first threshold, or awake if the sleep score is below a second threshold lower than the first threshold. If the sleep score falls between the first and second threshold, additional testing or confirmation (such as pushing interactive reminders to the patient) may be carried out to determine the sleep or awakening state. In addition or alternative to the physiological and functional signals, sleep or awakening state can be detected using data representing patient interaction with a mobile device such as the mobile device 140 or the wearable electronic device 120, such as patient reactions to alerts or notifications presented to the patient.

A pain level may be predicted for the detected physiological or functional state based on the sleep and awakening state, such by using the pain assessment module 657. In an example, a sleep parameter can be trended over time, and a pain level can be predicted based on the trend of the sleep parameter. For example, a sustained poor sleep quality such as increased sleep disturbance can indicate worsening of pain, or non-optimal or lack of effectiveness of present pain therapy.

At 940, the patient data received at 910, including for example the activity data, pain data, sleep date, patient reported outcome, may be stored in a cloud storage. Analysis results such as produced by one or more cloud-based services may also be stored in the cloud storage, including activity-pain correlations, correspondence between the activity scores and pain scores, sleep scores, pain predictions, among others.

At 950, the detected physiological or functional state and/or the pain prediction may be provided to a user or the patient, such as being presented on a user interface of the mobile device 140, the wearable electronic device 120, or the user terminal 160. In some examples, recommendations may be provided to the patient to make behavior change to promote pain relief. For example, the patient may be recommended to engage in or increase the engagement of the pain-free/pain-relieving activities and/or to avoid or reduce the identified pain-causing activities identified from step 930.

At 960, a pain therapy, such as a spinal-cord stimulation (SCS) therapy generated by the IPG 112, may be initiated or adjusted based on the pain prediction. In an example, a clinician may use a user terminal 160 to access the cloud-based services, and program the IPG 112 remotely such as by modifying one or more pain therapy parameters in the IPG 112.

Figure 10:
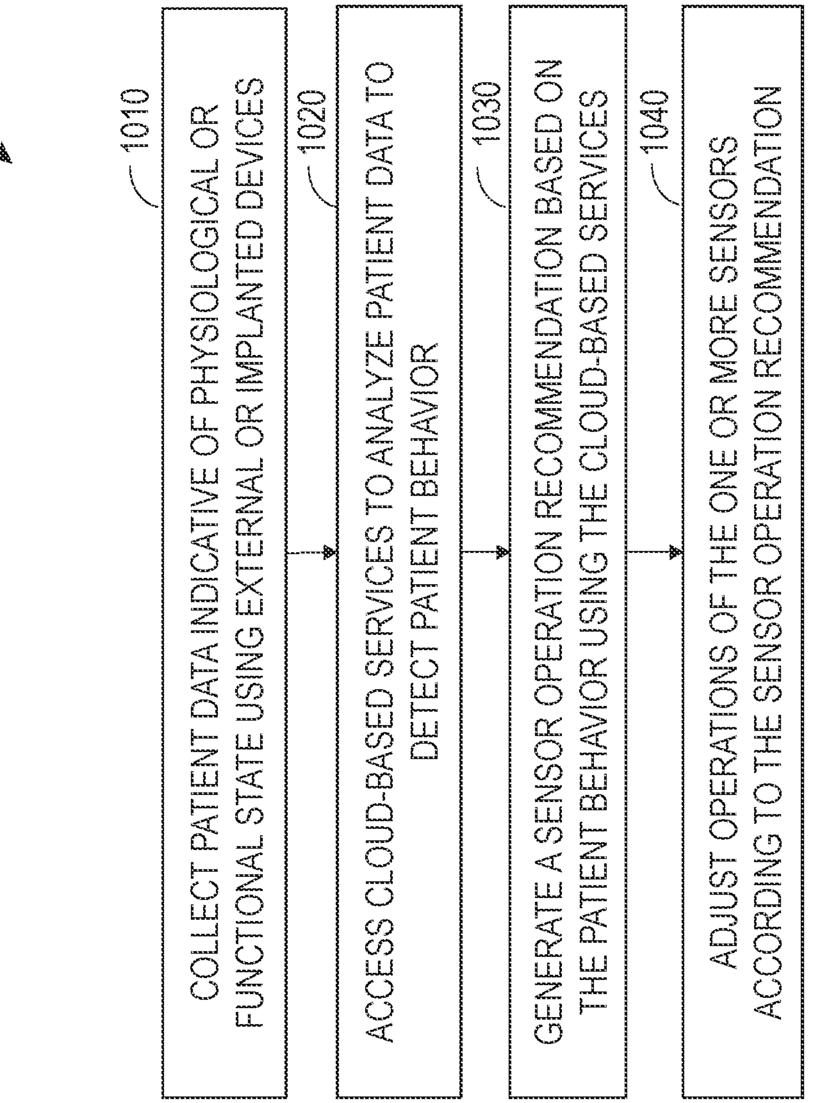
FIG. 10 illustrates generally an example of a method for remote monitoring of patient behavior, and adjusting operation of a device based on the patient behavior.

FIG. 10 illustrates, by way of example and not limitation, a method 1000 for remote monitoring of patient behavior, and adjusting operation of a device, such as the wearable electronic device 120, the mobile device 140, or the sensors in the IPG 112, based on the patient activity. The method 1000 may be implemented in and executed by, for example, the cloud-based patient monitoring system 700.

The method 1000 begins at step 1010, where patient data indicative of physiological or functional state of the patient may be collected using one or more implantable or external devices, such as the IPG 112, the wearable electronic device 120, or the mobile device 140. Similar to step 910 of the method 900, the patient data may include data collected by sensors from various devices, and patient reported outcome (PRO) such as received via a mobile app on the mobile device 140.

At 1020, cloud-based services, such as software implementations of algorithms for data analysis stored in the cloud-computing device 150 (or any of its variants such as cloud-computing device 750), may be accessed by an authorized user (e.g., the patient or a clinician) via a remote device, such as the wearable electronic device 120, the mobile device 140, or the user terminal 160. The cloud-based services may be used to detect a behavior of the patient at 920, such as patient engagement in physical activities, or a sleep or awakening state.

At 1030, a sensor operation recommendation can be generated based on the patient behavior. The recommendation may be generated using the cloud-based services for analyzing operating states of sensors or devices, as described above with reference to FIG. 7. In an example, the patient may be reminded to charge a battery of the wearable electronic device 120 powering one or more sensors the based on the detected patient behavior. For example, the reminders to charge the wearable electronic device 120 can be sent at times when it is least likely to collect important data or to perform physiological tracking, or at time prior to incidents where it is most desirable to avoid dead battery. For example, if it is desirable to collect data when the patient is in a particular functional state (e.g., during sleep) or being engaged in a particular physical activity, then a reminder can be provided to the patient to charge the wearable electronic device 120 at a specific time (e.g., at least one hour) prior to the anticipated functional state or the anticipated physical activity. In some examples, the reminder may be sent prior to a predicted physical state or the activity. In another example, the reminder may be sent in accordance with a physical activity schedule or a sleep schedule provided by the patient. In yet another example, the reminder may be generated based on historical device battery usage pattern and/or charging history.

In another example, the sensor operation recommendation may include selectively activating (switching on) or deactivating (switching off) a sensor to collect data from the patient, adjusting a data acquisition schedule for a sensor, or adjusting the sensor operation can include adjusting a sampling rate or data collection duration for one or more sensors.

In another example, a sensor anomaly can be detected using the data collected by a sensor. The sensor anomaly may be indicative of the wearable device being incorrectly worn, too loosely or too tightly worn or otherwise misplaced on the patient. The data quality controller 759 may compute a sensor data quality score from a physiological signal sensed by the sensor, such as using a template-matching method. If the sensor data quality score exceeds a threshold, the wearable device is deemed properly worn. If the sensor data quality score falls below the threshold, an alert such a notification may be provided to the user to check if the wearable device is properly worn. In some examples, a recommendation to correct misplacement of the wearable device can be provided to patient. In some examples, sensor anomaly can be cross-validated using measurements obtained from two or more sensors. For example, if two different sensors (e.g., a PPG sensor in the wearable electronic device 140, and a heart rate sensor in the IPG 112) both detect abnormal heart rates indicative of improper wearing of the wearable electronic device on the patient, then the anomaly is confirmed, and an alert can be provided to the user. If the detected heart rates from the two sensors are inconsistent, then the sensor anomaly is not confirmed; in some examples, further validation such as a third heart rate sensor may be used to validate proper device wearing on the patient. In some examples, sensor anomaly detected using the sensor data (e.g., improper wearing of the wearable electronic device 140) may be confirmed by the patient.

At 1040, operations of the one or more sensors, such as the sensor in the IPG, the wearable electronic device 120, or the mobile device 140, may be adjusted according to the sensor operation recommendations. This may include, for example, the clinician adjusting the sensor settings in the IPG 112 via the user terminal 160, or the patient charging the battery of the devices at recommended time, correcting misplacement or improper wearing of the devices on the body, or adjusting the sensor settings in the wearable electronic device 120 or the mobile device 140.

Figure 11:
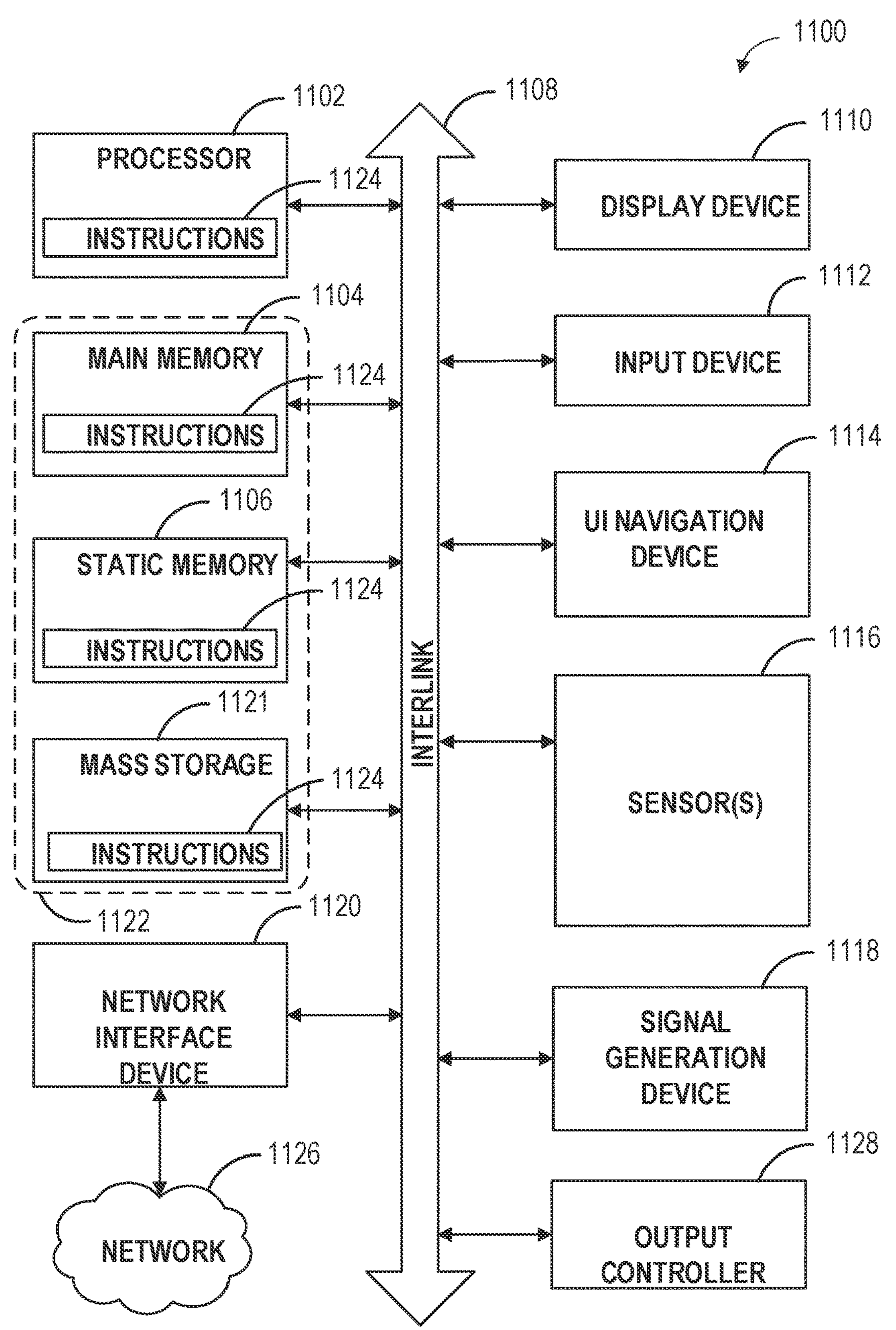
FIG. 11 illustrates generally a block diagram of an example machine upon which any one or more of the techniques (e.g., methodologies) discussed herein may perform.

FIG. 11 illustrates generally a block diagram of an example machine 1100 upon which any one or more of the techniques (e.g., methodologies) discussed herein may perform. Portions of this description may apply to the computing framework of various portions of the cloud-computing device 350 or any of its variants such as cloud-computing devices 550, 650, or 750.

In alternative embodiments, the machine 1100 may operate as a standalone device or may be connected (e.g., networked) to other machines. In a networked deployment, the machine 1100 may operate in the capacity of a server machine, a client machine, or both in server-client network environments. In an example, the machine 1100 may act as a peer machine in peer-to-peer (P2P) (or other distributed) network environment. The machine 1100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1100 may include a hardware processor 1102 (e.g., a central processing unit (CPU), a graphics processing unit (GPU), a hardware processor core, or any combination thereof), a main memory 1104 and a static memory 1106, some or all of which may communicate with each other via an interlink (e.g., bus) 1108. The machine 1100 may further include a display unit 1110 (e.g., a raster display, vector display, holographic display, etc.), an alphanumeric input device 1112 (e.g., a keyboard), and a user interface (UI) navigation device 1114 (e.g., a mouse). In an example, the display unit 1110, input device 1112 and UI navigation device 1114 may be a touch screen display. The machine 1100 may additionally include a storage device (e.g., drive unit) 1116, a signal generation device 1118 (e.g., a speaker), a network interface device 1120, and one or more sensors 1121, such as a global positioning system (GPS) sensor, compass, accelerometer, or other sensor. The machine 1100 may include an output controller 1128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1116 may include a machine readable medium 1122 on which is stored one or more sets of data structures or instructions 1124 (e.g., software) embodying or utilized by any one or more of the techniques or functions described herein. The instructions 1124 may also reside, completely or at least partially, within the main memory 1104, within static memory 1106, or within the hardware processor 1102 during execution thereof by the machine 1100. In an example, one or any combination of the hardware processor 1102, the main memory 1104, the static memory 1106, or the storage device 1116 may constitute machine readable media.

While the machine readable medium 1122 is illustrated as a single medium, the term "machine readable medium" may include a single medium or multiple media (e.g., a centralized or distributed database, and/or associated caches and servers) configured to store the one or more instructions 1124.

The term "machine readable medium" may include any medium that is capable of storing, encoding, or carrying instructions for execution by the machine 1100 and that cause the machine 1100 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1124 may further be transmitted or received over a communications network 1126 using a transmission medium via the network interface device 1120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1120 may include one or more physical jacks (e.g., Ethernet, coaxial, or phone jacks) or one or more antennas to connect to the communications network 1126. In an example, the network interface device 1120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1100, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for remote monitoring of a patient with an implantable device for pain management, the system comprising:

one or more sensors configured to sense physiological or functional information from the patient;

a cloud-computing device communicatively coupled to the one or more sensors, the cloud-computing device configured to receive patient data including the sensed physiological or function information, and to provide cloud-based services including:

storing the received patient data in a cloud storage;

detecting a patient behavior including a physical activity level or a physical activity schedule using the received patient data; and generating a sensor operation recommendation based on the detected patient behavior; and a remote device configured to:

access the cloud storage and the cloud-based services via a communication network, and generate a sensor-usage trend indicative of a temporal pattern of a user's interaction with at least one of the one or more sensors, the sensor-usage trend further including a user's battery charging pattern representing a duration of a battery-powered device being charged by the user during a given period;

display concurrently, on a user interface, a graphical representation of a temporal relationship between the sensor-usage trend over a time period and a trend of the physical activity level or the physical activity schedule over the same time period, and the sensor operation recommendation; and automatically adjust operations of the one or more sensors, including transitioning the one or more sensors between different operational states with respect to data acquisition, in accordance with the sensor operation recommendation.

2. The system of claim 1, wherein the cloud-based services further include predicting a pain level using the received patient data, and the remote device is configured to generate a control signal to the implantable device to initiate or adjust a neuromodulation therapy for pain management in accordance with the predicted pain.

3. The system of claim 1, wherein the cloud-computing device is configured to:

detect the patient behavior including detecting a sleep state or receiving a sleep schedule from the patient; and generate the sensor operation recommendation based on the sleep state or the sleep schedule.

4. The system of claim 1, wherein the one or more sensors are powered by a rechargeable battery in the implantable device or in a mobile device, and wherein the cloud-computing device is configured to generate the sensor operation recommendation including a recommendation to charge the rechargeable battery based on the detected patient behavior.

5. The system of claim 4, wherein the cloud-computing device is configured to generate the recommendation to charge the rechargeable battery further based on a battery level of the rechargeable battery.

6. The system of claim 4, wherein the cloud-computing device is further configured to generate the recommendation to charge the rechargeable battery further based on the sensor-usage trend.

7. The system of claim 1, wherein the cloud-computing device is configured to generate the sensor operation recommendation including a recommendation to activate or deactivate the one or more sensors based on the detected patient behavior.

8. The system of claim 1, wherein the cloud-computing device is configured to generate the sensor operation recommendation including a recommendation to adjust a data acquisition schedule or a data sampling rate for the one or more sensors based on the detected patient behavior.

9. The system of claim 1, wherein the cloud-computing device is further configured to:

detect a sensor anomaly using the sensed physiological or function information, the sensor anomaly indicating a misplacement of the one or more sensors on the patient; and provide an indication of the detected sensor anomaly to the patient or a user.

10. The system of claim 1, wherein the remote device includes a mobile device configured to communicate with the implantable device, the mobile device operable by the patient and configured to collect the patient data including one or more of neuromodulation therapy data for pain management; patient reported outcome (PRO) provided by the patient; or physiological or functional data from the patient.

11. A method for remote monitoring of a patient with an implantable device for pain management via a cloud-based system comprising a cloud-computing device, the method comprising:

via the cloud-computing device, receiving patient data including physiological or function information sensed by one or more sensors included in the implantable device or in one or more external devices, and providing cloud-based services including:

storing the received patient data in a cloud storage;

detecting a patient behavior including a physical activity level or a physical activity schedule using the received patient data; and generating a sensor operation recommendation based on the detected patient behavior; and via a remote device communicatively coupled to the cloud-computing device:

accessing the cloud storage and the cloud-based services;

generating a sensor-usage trend indicative of a temporal pattern of a user's interaction with at least one of the one or more sensors, the sensor-usage trend further including a user's battery charging pattern representing a duration of a battery-powered device being charged by the user during a given period;

displaying concurrently, on a user interface, a graphical representation of a temporal relationship between the sensor-usage trend over a time period and a trend of the physical activity level or the physical activity schedule over the same time period, and the sensor operation recommendation; and automatically adjusting operations of the one or more sensors, including transitioning the one or more sensors between different operational states with respect to data acquisition, in accordance with the sensor operation recommendation.

12. The method of claim 11, further comprising:

predicting a pain level using the received patient data; and initiating or adjusting a neuromodulation therapy in accordance with the predicted pain level.

13. The method of claim 11, wherein the patient data include one or more of:

physiological or functional data collected by one or more sensors;

neuromodulation therapy data collected by the implantable device; or patient reported outcome (PRO) collected by a mobile device.

14. The method of claim 11, wherein:

detecting the patient behavior includes detecting a sleep state or receiving a sleep schedule from the patient; and generating the sensor operation recommendation is based on the sleep state or the sleep schedule.

15. The method of claim 11, wherein generating the sensor operation recommendation includes generating a recommendation to charge a rechargeable battery powering the one or more sensors based on one or more of the detected patient behavior, a battery level of the rechargeable battery, or the generated sensor-usage trend.

16. The method of claim 11, wherein generating the sensor operation recommendation includes one or more of recommendations of, based on the detected patient behavior:

activating or deactivating the one or more sensors;

adjusting a data acquisition schedule for the one or more sensors; or adjusting a data sampling rate for the one or more sensors.

17. The method of claim 11, comprising:

detecting a sensor anomaly using the sensed physiological or function information, the sensor anomaly indicating a misplacement of the one or more sensors on the patient; and providing an indication of the detected sensor anomaly to the patient or a user.

18. The method of claim 17, wherein:

detecting the sensor anomaly includes detecting an improper wearing of a wearable electronic device on the patient; and generating the sensor operation recommendation includes a recommendation to adjust the wearing of the wearable electronic device.

19. The system of claim 4, wherein the sensor-usage trend concurrently displayed on the user interface includes at least one of a battery status trend or a battery charging pattern associated with the rechargeable battery powering the one or more sensors.

20. The method of claim 15, wherein the sensor-usage trend concurrently displayed on the user interface includes at least one of a battery status trend or a battery charging pattern associated with the rechargeable battery powering the one or more sensors.

* * * * *